(12) United States Patent
Tang et al.

(10) Patent No.: US 11,389,446 B2
(45) Date of Patent: Jul. 19, 2022

(54) THERANOSTIC AGENTS

(71) Applicant: THE HONG KONG UNIVERSITY OF SCIENCE AND TECHNOLOGY, Hong Kong (CN)

(72) Inventors: Benzhong Tang, Hong Kong (CN); Dan Ding, Hong Kong (CN); Ji Qi, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 16/614,141

(22) PCT Filed: May 14, 2018

(86) PCT No.: PCT/CN2018/086716
§ 371 (c)(1),
(2) Date: Nov. 15, 2019

(87) PCT Pub. No.: WO2018/210206
PCT Pub. Date: Nov. 22, 2018

(65) Prior Publication Data
US 2020/0147078 A1 May 14, 2020

Related U.S. Application Data

(60) Provisional application No. 62/603,057, filed on May 17, 2017.

(51) Int. Cl.
| | | |
|---|---|---|
| *C07D 513/04* | (2006.01) | |
| *A61K 31/4985* | (2006.01) | |
| *A61K 41/00* | (2020.01) | |
| *A61K 49/22* | (2006.01) | |

(52) U.S. Cl.
CPC ...... *A61K 31/4985* (2013.01); *A61K 41/0052* (2013.01); *A61K 49/221* (2013.01); *C07D 513/04* (2013.01)

(58) Field of Classification Search
CPC .................................................. C07D 513/04
See application file for complete search history.

(56) References Cited

FOREIGN PATENT DOCUMENTS

| | | |
|---|---|---|
| CN | 103842472 A | 6/2014 |
| CN | 106147755 A | 11/2016 |

OTHER PUBLICATIONS

Qi et al. ACS Nano 2017, 11, 7, 7177-7188.*
Corrected Version International Search Report for PCT/CN2018/086716 dated Sep. 20, 2019.

* cited by examiner

*Primary Examiner* — Brian E Mcdowell
(74) *Attorney, Agent, or Firm* — Nath, Goldberg & Meyer; Joshua B. Goldberg

(57) ABSTRACT

A theranostic agent can be used in both photoacoustic imaging (PAI) and photothermal therapy (PTT) applications. The theranostic agent can include a small molecule, organic compound with absorption in the near-infrared (NIR) interrogation window (700-900 nm). The compound can be a biocompatible organic nanoparticle (ONP). The theranostic agent can be effectively used in PAI and PAI-guided PTT applications. The theranostic agent can be administered to a patient to locate a tumor site in the patient using in vivo imaging techniques. Once the tumor site has been determined, the tumor site can be irradiated with near-infrared light to stop or inhibit the growth of the tumor. An exemplary theranostic agent is provided below

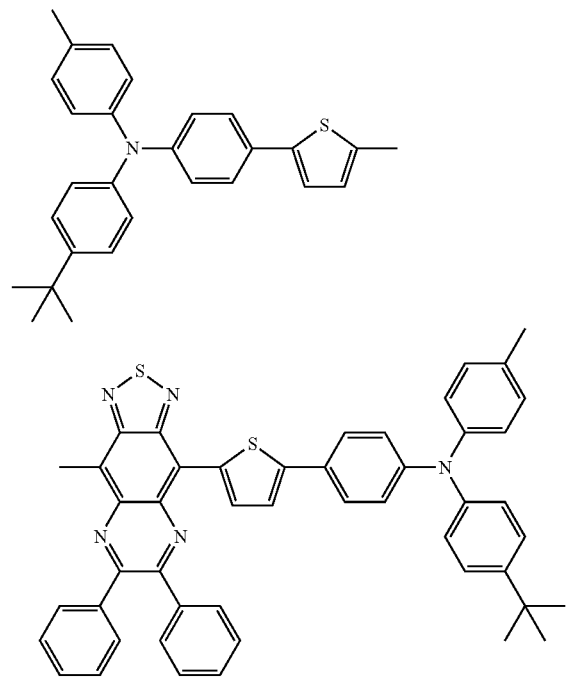

1 Claim, 11 Drawing Sheets

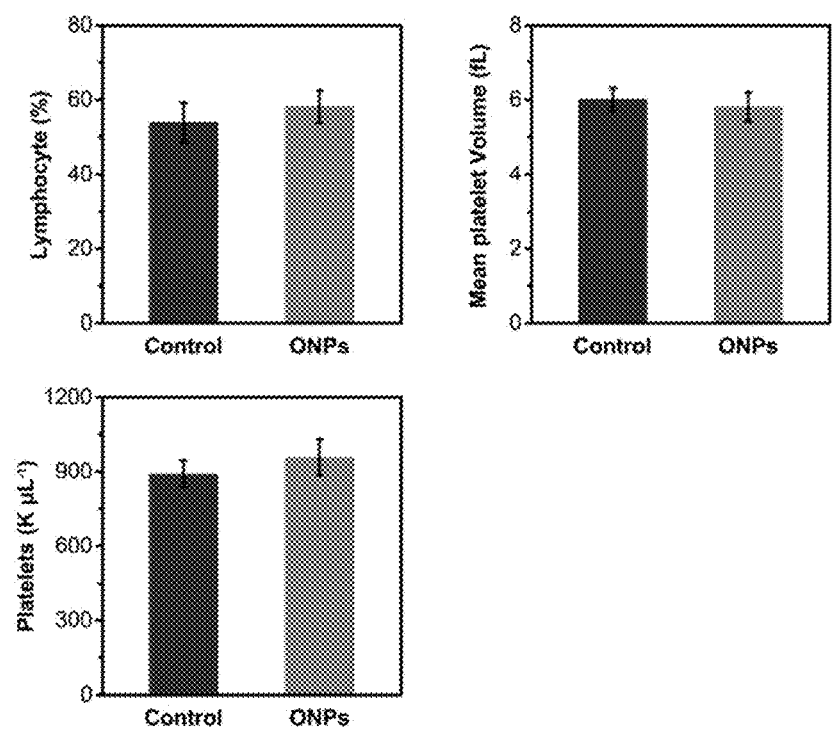
FIGs. 14B (con't)

THERANOSTIC AGENTS

FIELD

The present subject matter relates generally to a series of organic, small molecule compounds with absorption in the near-infrared (NIR) interrogation window (700-900 nm) and their applications in photoacoustic imaging (PAI) and photothermal therapy (PTT).

BACKGROUND

The emergence of photo-theranostic agents has opened a new door for cancer research. Theranostic agents can facilitate integration of real-time diagnosis and in-situ phototherapeutic capabilities in one platform. Among versatile light-triggered diagnostic/therapeutic techniques, photoacoustic imaging (PAI) associated with photothermal therapy (PTT) is particularly effective in accurately probing tumor location and effectively inhibiting tumor growth, with minimal side effect to normal tissue. PAI is a very promising noninvasive molecular imaging approach that combines deep tissue penetration and high resolution of ultrasound imaging with high contrast of optical imaging. The therapeutic technique that typically accompanies PAI is PTT, as PAI is used primarily to detect the photothermally generated ultrasound signal. The most vital prerequisite of PAI/PTT applications is to employ efficient contrast agents with strong absorption in the near-infrared (NIR) interrogation window (700-900 nm), since NIR light is known to penetrate much deeper tissue and cause less photodamage to a living body.

A variety of nanomaterials, such as metal nanomaterials (e.g., gold, and silver nanostructures), carbon nanomaterials (e.g., carbon nanotubes, and graphene), transition metal dichalcogenides (e.g., $MoS_2$, $WS_2$, and $Ag_2S$), and organic material-based nanoparticles, have been extensively investigated as PAI/PTT agents. Unlike inorganic nanoagents, organic materials, e.g., polymers and small molecules, offer advantages of outstanding biocompatibility, potential biodegradability, and easy processability. Accordingly, semiconducting polymer nanoparticles (SPNs) have recently been explored as contrast agents for PAI, as well as PTT applications with superb performance. However, development of organic small molecules applicable for PAI/PTT has been less extensive even though organic small molecules have the advantage of a well-defined chemical structure, high purity, good reproducibility, facile modification, and easy processibility. One challenge typically associated with some organic small molecules involves instability of the molecules in PAI/PTT applications, which to date has limited development in this area.

Some conventional cyanine dyes have been investigated and used as intermediates for light-mediated biomedical applications in clinics. For example, indocyanine green (ICG), an ionic compound with strong absorption in the NIR spectral region of 700-850 nm, has been approved by the Food and Drug Administration (FDA) for clinical use, highlighting the potential of organic small molecules for clinical translation and practical applications. These cyanine dyes, however, suffer from the problems of modification difficulty and poor stability, which may lead to safety problems and untrusted theranostic outcomes. For example, many cyanine dyes are prone to decomposition by reactive oxygen/nitrogen species (RONS). As such, many cyanine dyes are useful as sensitive probes for detecting RONS in a living body. The alternatively arranged single and double bonds in cyanine dyes are easily oxidized by the highly reactive RONS, which results in the decrease or disappearance of featured NIR absorption and fluorescence signals. While utilization of the reactive feature of cyanine dyes for ratiometric sensing of RONS is reasonable, the instability of cyanine dyes would create serious problems in PAI/PTT applications, such as misleading PAI signals, impaired PTT treatment efficacy, and harmful side effects caused by in vivo decomposition.

Many of the currently available NIR-absorbing organic small molecules face various challenges, including, photothermal instability, photobleaching, and susceptibility to RONS decomposition.

Accordingly, the development of highly stable NIR organic small molecular agents for effective PAI/PTT applications is desired.

SUMMARY

The present subject matter relates to a theranostic agent that can be used in both photoacoustic imaging (PAI) and photothermal therapy (PTT) applications. The theranostic agent can include a small molecule, organic compound with absorption in the near-infrared (NIR) interrogation window (700-900 nm). The compound can be a biocompatible organic nanoparticle (ONP). The theranostic agent can be administered to a patient to locate a tumor site in the patient using photoacoustic imaging. Once the tumor site has been determined, the tumor site can be irradiated with near-infrared light which, when combined with the present compounds, can stop or inhibit the growth of the tumor.

In an embodiment, the compound has:

a donor unit selected from the group consisting of

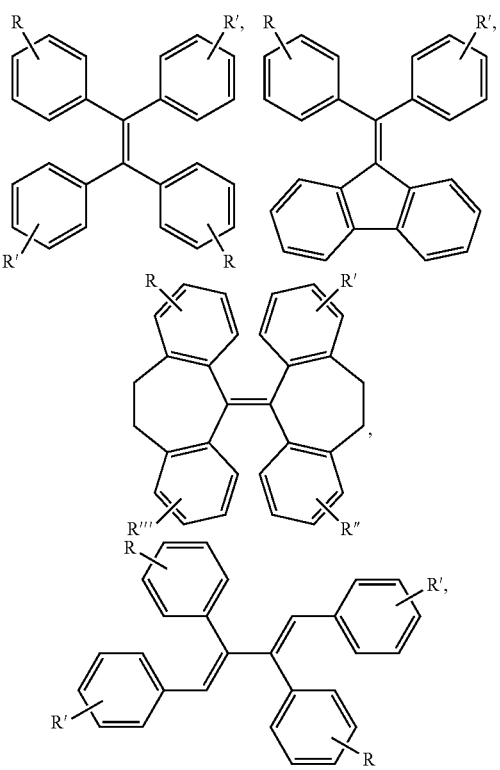

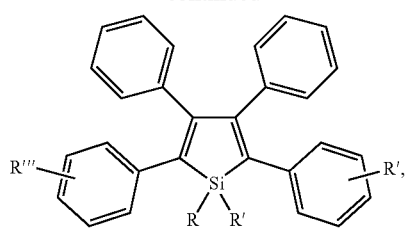
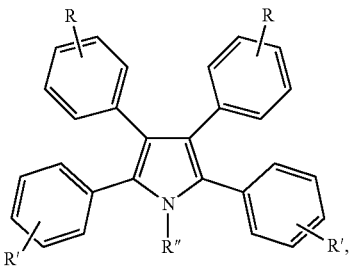
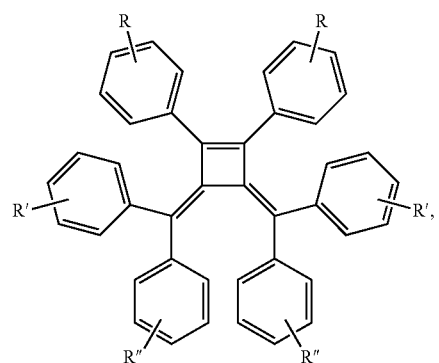
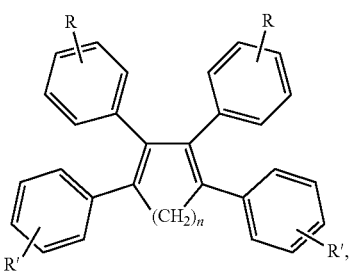
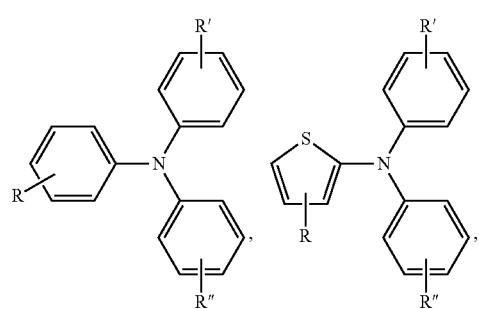
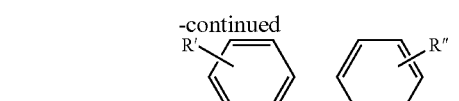
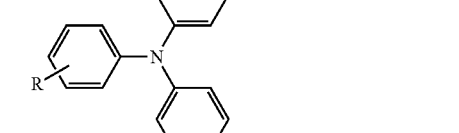
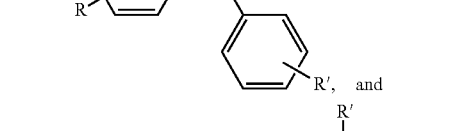
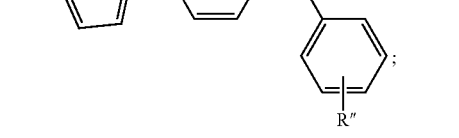

and an acceptor unit (A) selected from the group consisting of:

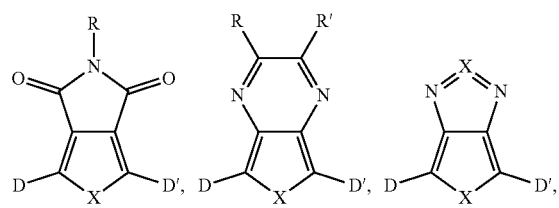

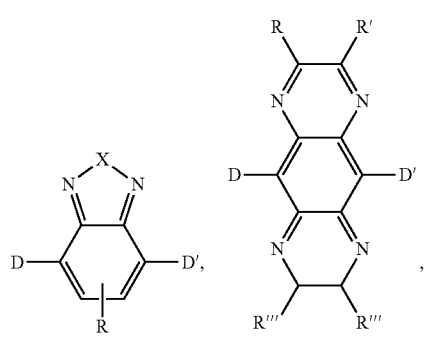

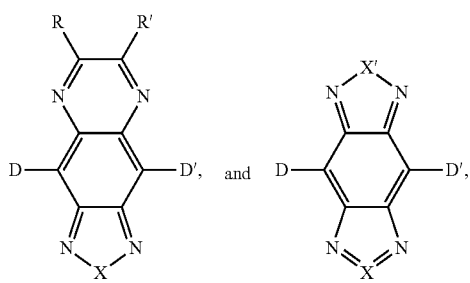

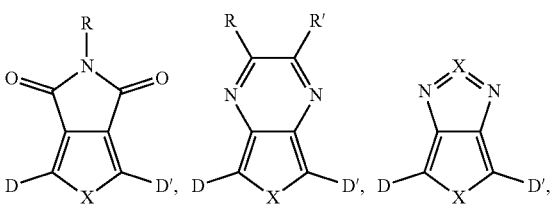

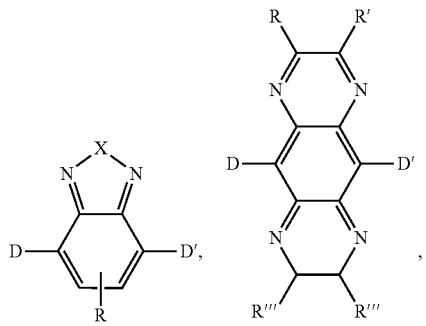

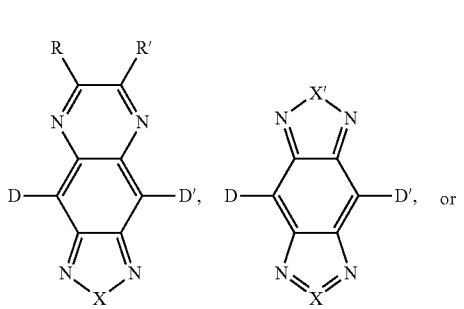

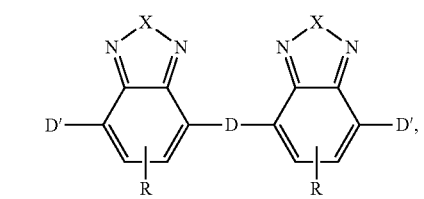

wherein D and D' represent the donor unit;

wherein the compound has a structural arrangement in a form selected from the group consisting of D-A, D-A-D, A-D-A, D-D-A-D-D, A-A-D-A-A, D-A-D-A-D, A-D-A-D-A, wherein A represents the acceptor unit;

wherein each of X and X' is selected from the group consisting of O, S, Se, and Te;

wherein each of R, R', R" R'", or R"" is unsubstituted or substituted and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group; and wherein at least one of R, R', R" R'", or R"" is a terminal functional group having a substituent independently selected from the group consisting of $N_3$, NCS, SH, $NH_2$, COOH, alkyne, N-hydroxysuccinimide ester, maleimide, hydrazide, nitrone group, —CHO, —OH, halide, and a charged ionic group; and wherein at least one of R, R', R" R'", and R"" is other than H.

In a further embodiment, the compound has one of the following structural formulae:

wherein each of X and X' is selected from the group consisting of O, S, Se, and Te;

wherein each of D and D' is selected from the group consisting of

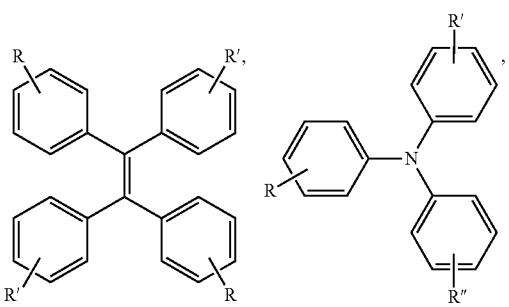

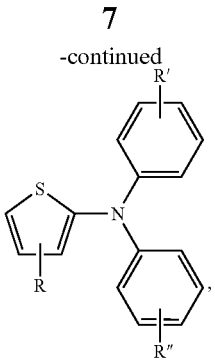

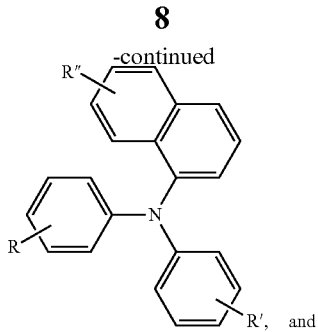

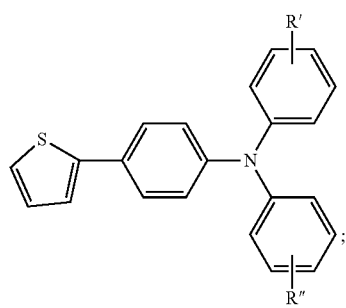

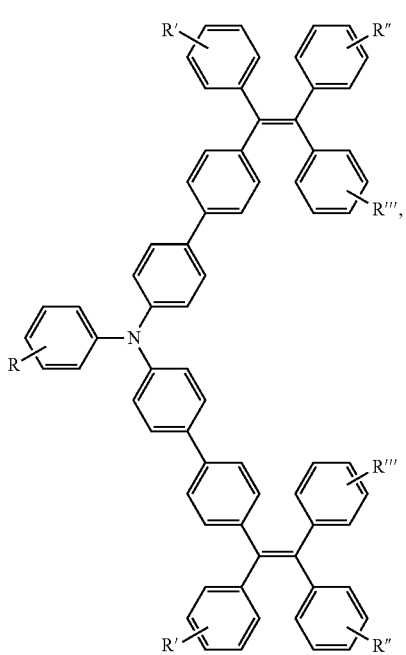

wherein each of R, R', R", and R'" is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R", and R'" is a terminal functional group having a substituent independently selected from the group consisting of $N_3$, NCS, SH, $NH_2$, COOH, alkyne, N-hydroxysuccinimide ester, maleimide, hydrazide, nitrone group, —CHO, —OH, halide, and a charged ionic group; and wherein at least one of R, R', R", and R'" is other than H.

In an embodiment, the compound has the following structural formula:

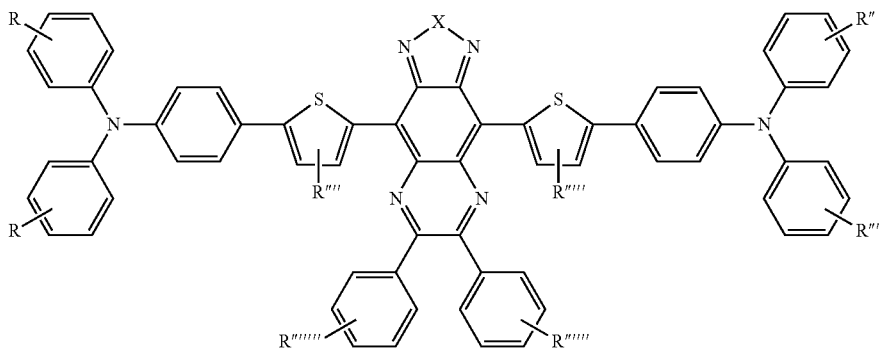

wherein X is selected from the group consisting of O, S, Se, and Te;

wherein each of R, R' R", R'", R"" R""', R""", and R"""" is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R" R'", R"", R""', R""", and R"""" is a terminal functional group having a substituent independently selected from the group consisting of $N_3$, NCS, SH, $NH_2$, COOH, alkyne, N-Hydroxysuccinimide ester, maleimide, hydrazide, nitrone group, —CHO, —OH, halide, and a charged ionic group; and wherein at least one of R, R' R", R'", R"" R""', R""", and R"""" is other than H.

In an embodiment, the compound has the following structural formula:

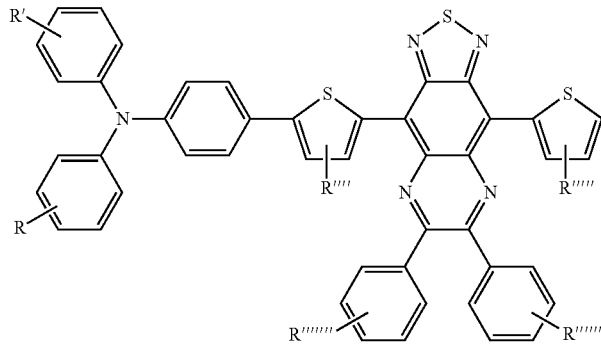

wherein each of R, R' R", R'", R"", R""', R""", and R"""" is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R", R'", R"", R""', R""", and R"""" is a terminal functional group having a substituent independently selected from the group consisting of $N_3$, NCS, SH, $NH_2$, COOH, alkyne, N-Hydroxysuccinimide ester, maleimide, hydrazide, nitrone group, —CHO, —OH, halide, and a charged ionic group; and wherein at least one of R, R', R" R'", R"", R""', R""", and R"""" is other than H.

In an embodiment, an exemplary compound is:

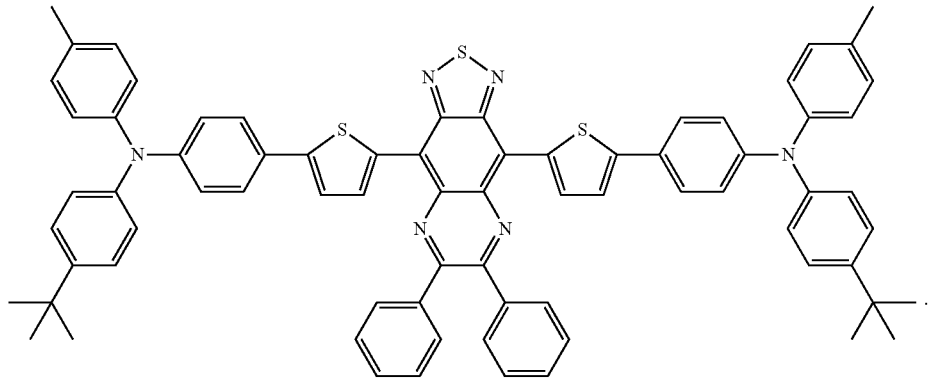

TPA-T-TQ

BRIEF DESCRIPTION OF DRAWINGS

Various embodiments will now be described in detail with reference to the accompanying drawings.

DETAILED DESCRIPTION

Figures 1, 2:
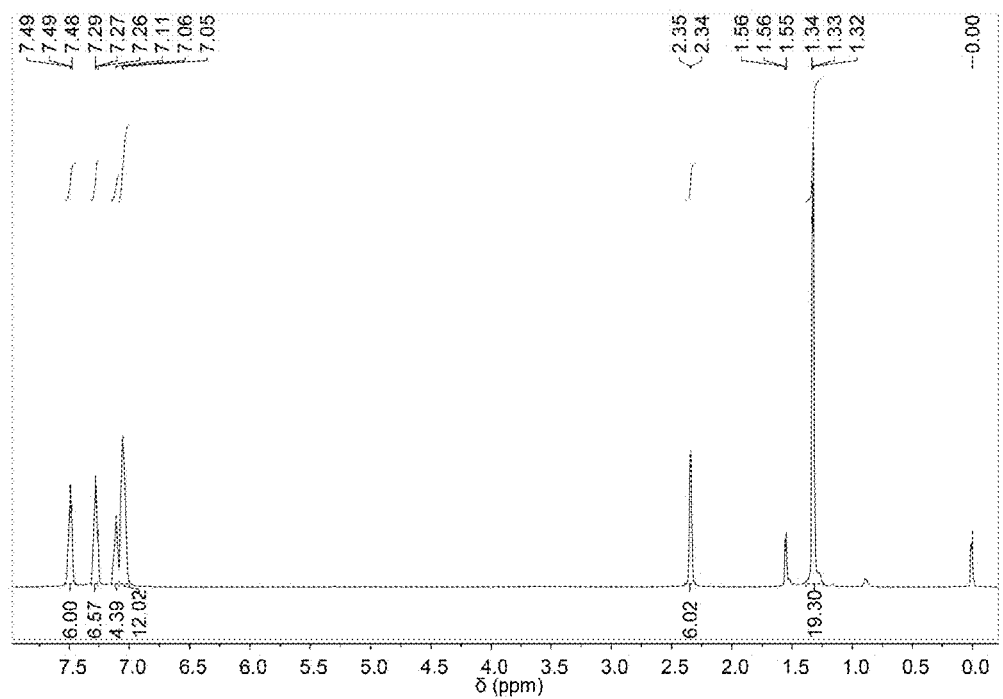
FIG. 1 depicts the $^1$H NMR spectrum of compound 10 in $CDCl_3$.
FIG. 2 depicts the $^{13}$C NMR spectrum of compound 10 in $CDCl_3$.

The following definitions are provided for the purpose of understanding the present subject matter and for constructing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

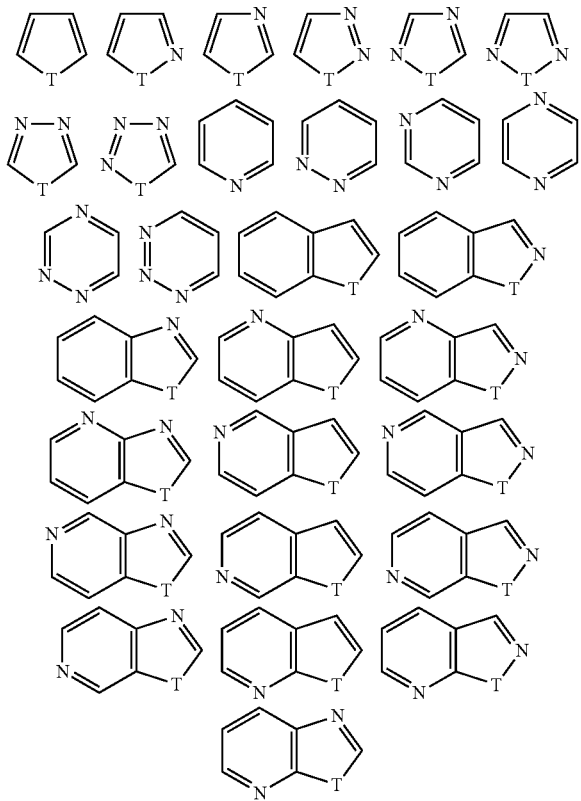

where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinox-alyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

As used herein, "halo" or "halogen" refers to fluoro, chloro, bromo, and iodo. As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-40 alkyl group), for example, 1-30 carbon atoms (i.e., C1-30 alkyl group). In some embodiments, an alkyl group can have 1 to 6 carbon atoms, and can be referred to as a "lower alkyl group." Examples of lower alkyl groups include methyl, ethyl, propyl (e.g., n-propyl and z'-propyl), and butyl groups (e.g., n-butyl, z'-butyl, sec-butyl, ten-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In some embodiments, alkenyl groups can be substituted as described herein. An alkenyl group is generally not substituted with another alkenyl group, an alkyl group, or an alkynyl group.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl." In certain embodiments, an aryl group is substituted with another aryl group and can be referred to as a biaryl group. Each of the aryl groups in the biaryl group can be substituted as disclosed herein.

As used herein, a "donor" material refers to an organic material, for example, an organic nanoparticle material, having holes as the majority current or charge carriers.

As used herein, an "acceptor" material refers to an organic material, for example, an organic nanoparticle material, having electrons as the majority current or charge carriers.

As used herein, a "theranostic agent" refers to an organic material, for example, an organic nanoparticle material, having both diagnostic and therapeutic capabilities.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Theranostic Agents

The present subject matter contemplates theranostic agents, or agents useful for both diagnostic and therapeutic purposes. A theranostic agent, as contemplated herein, can include at least one small molecule organic compound with absorption in the near-infrared (NIR) interrogation window (700-900 nm). The compound can be an organic nanoparticle (ONP). The theranostic agents described herein can provide ideal contrast agents for light triggered diagnostic/therapeutic techniques, such as photoacoustic imaging (PAI) associated with photothermal therapy (PTT). The theranostic agents described herein demonstrate excellent thermal and photothermal stabilities, as well as significant resistance to photobleaching and RONS. The theranostic agents described herein further exhibit excellent photothermal conversion performance when exposed to NIR light.

In an embodiment, the present theranostic agent is a small molecule, organic compound that has:

a donor unit selected from the group consisting of

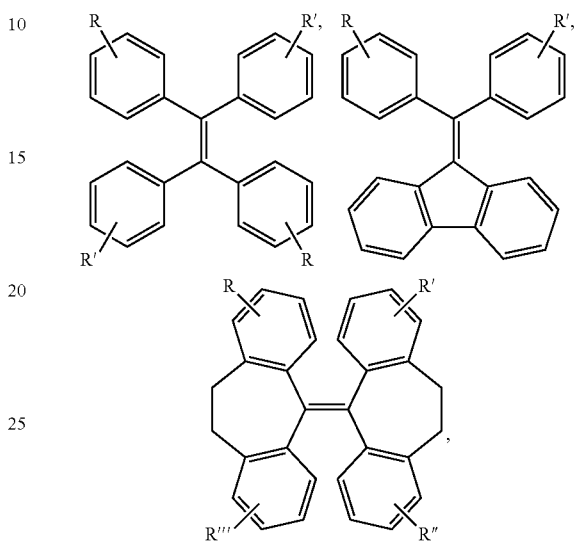

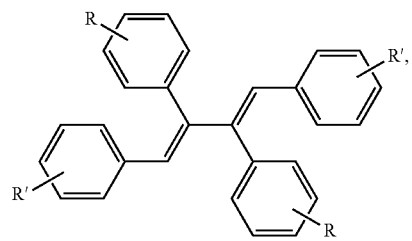

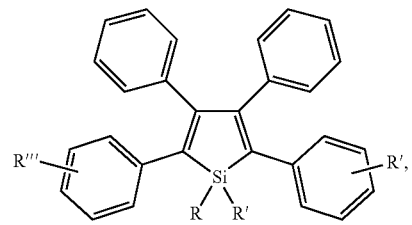

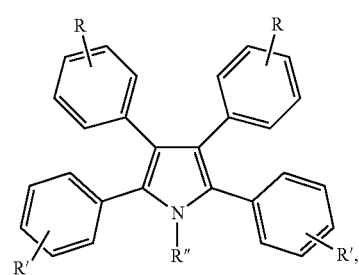

-continued
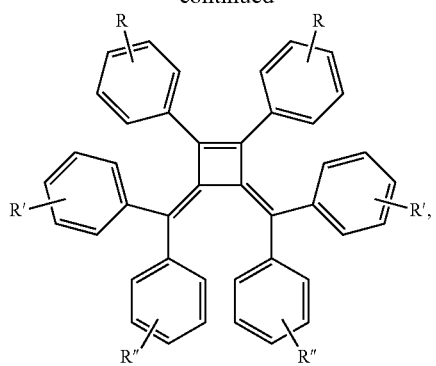
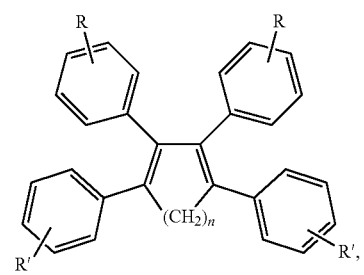
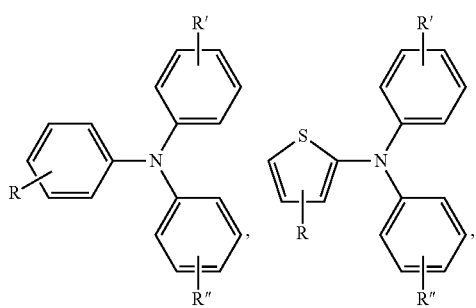
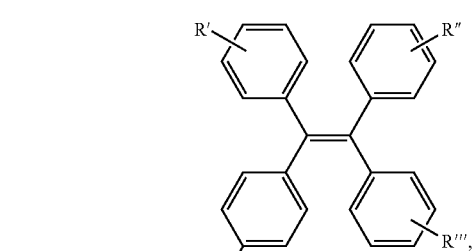
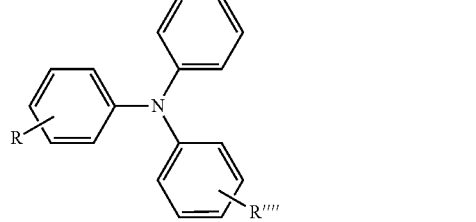
-continued
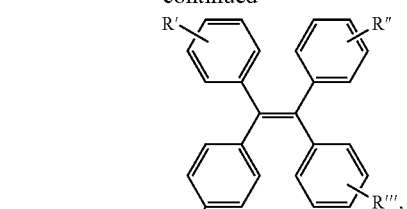
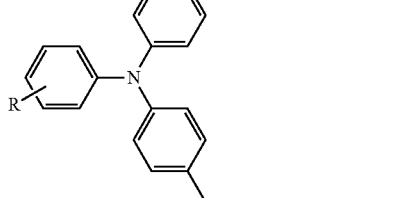
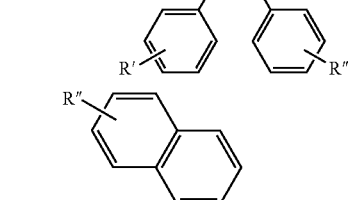
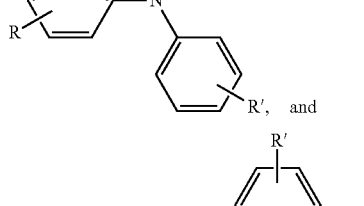
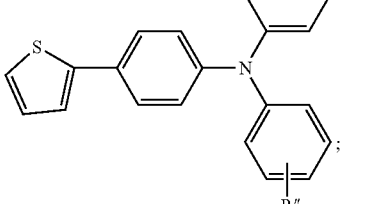, and
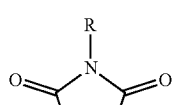
and
an acceptor unit (A) selected from the group consisting of:
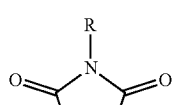 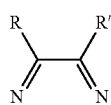 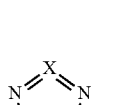

-continued

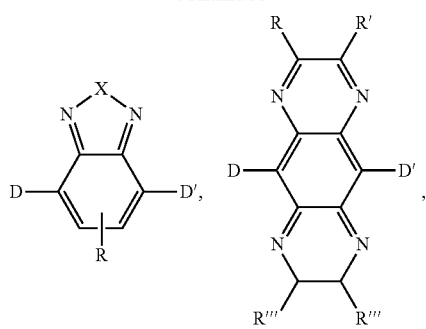

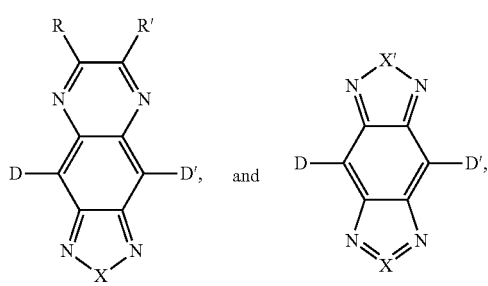

wherein the compound is arranged in a form selected from the group consisting of D-A, D-A-D, A-D-A, D-D-A-D-D, A-A-D-A-A, D-A-D-A-D, A-D-A-D-A, wherein D and D' represent the donor unit;

wherein A represents the acceptor unit;

wherein each of X and X' is selected from the group consisting of O, S, Se, and Te;

wherein each of R, R', R" R''', or R"" is unsubstituted or substituted and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group; and wherein at least one of R, R', R" R''', or R"" is a terminal functional group having a substituent independently selected from the group consisting of $N_3$, NCS, SH, $NH_2$, COOH, alkyne, N-hydroxysuccinimide ester, maleimide, hydrazide, nitrone group, —CHO, —OH, halide, and a charged ionic group; and wherein at least one of R, R', R" R''', and R"" is other than H.

In a further embodiment, the compound has one of the following structural formulae:

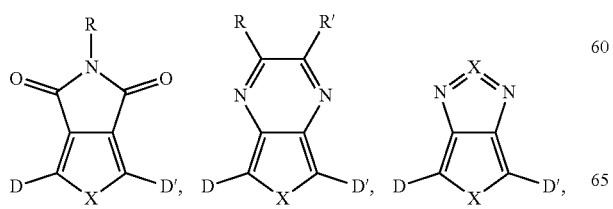

-continued

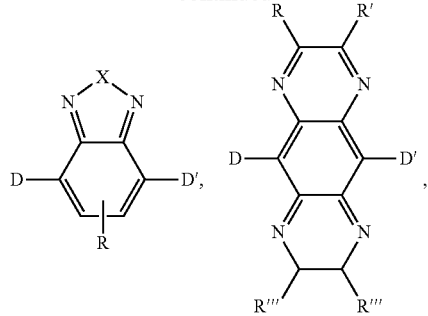

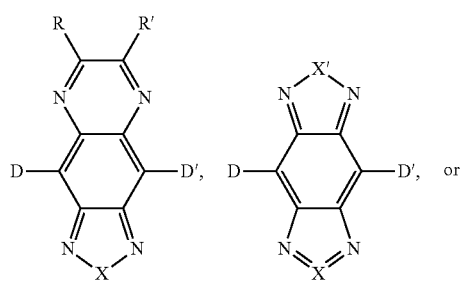

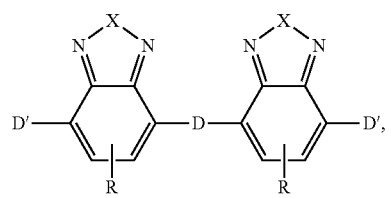

wherein each of X and X' is selected from the group consisting of O, S, Se, and Te;

wherein each of D and D' is selected from the group consisting of

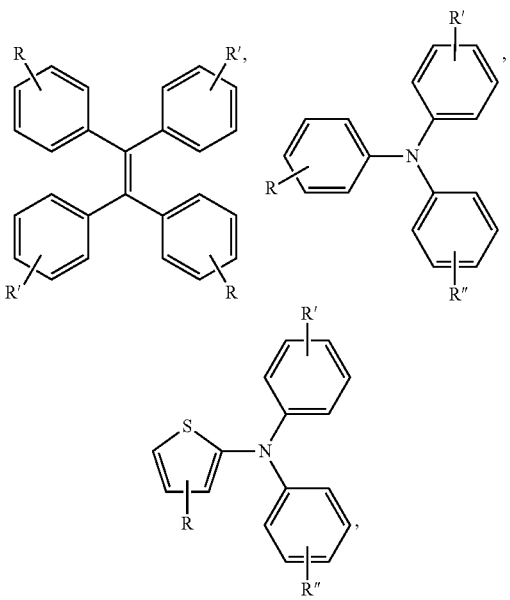

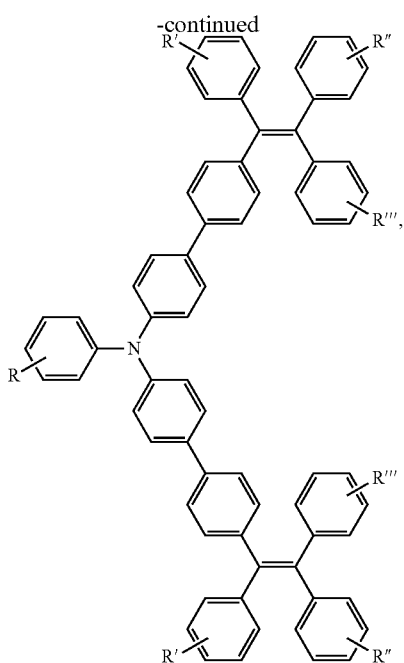

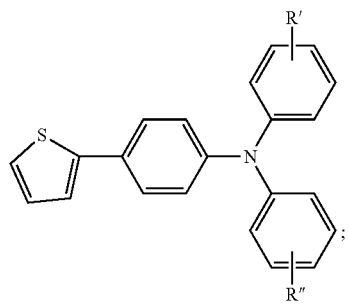

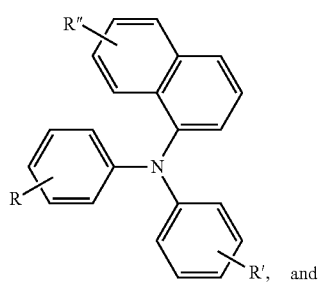 and wherein each of R, R', R", and R''' is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R", and R''' is a terminal functional group having a substituent independently selected from the group consisting of $N_3$, NCS, SH, $NH_2$, COOH, alkyne, N-hydroxysuccinimide ester, maleimide, hydrazide, nitrone group, —CHO, —OH, halide, and a charged ionic group; and wherein at least one of R, R', R", and R''' is other than H.

In an embodiment, the compound has the following structural formula:

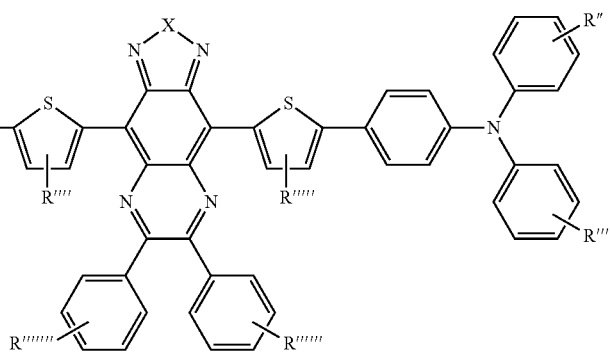

wherein X is selected from the group consisting of O, S, Se, and Te;

wherein each of R, R' R", R'", R"" R""', R"""", and R""""' is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R" R'", R"", R""', R"""", and R""""' is a terminal functional group having a substituent independently selected from the group consisting of $N_3$, NCS, SH, $NH_2$, COOH, alkyne, N-Hydroxysuccinimide ester, maleimide, hydrazide, nitrone group, —CHO, —OH, halide, and a charged ionic group; and wherein at least one of R, R' R", R'", R"" R""', R"""", and R""""' is other than H.

In an embodiment, the compound has the following structural formula:

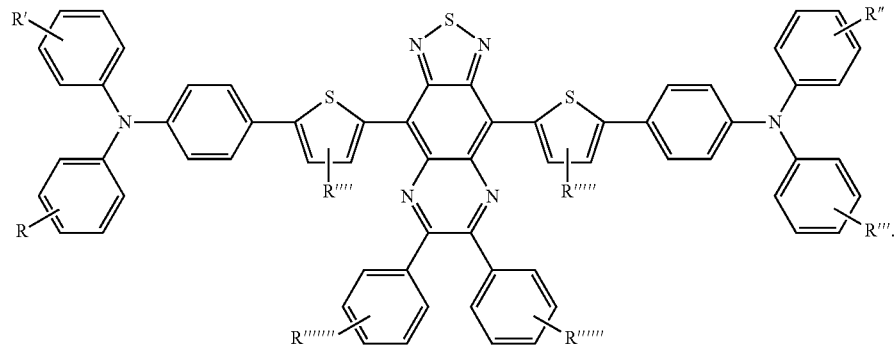

wherein each of R, R' R", R'", R"", R""', R"""", and R""""' is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group;

wherein at least one of R, R', R", R'", R"", R""', R"""", and R""""' is a terminal functional group having a substituent independently selected from the group consisting of $N_3$, NCS, SH, $NH_2$, COOH, alkyne, N-Hydroxysuccinimide ester, maleimide, hydrazide, nitrone group, —CHO, —OH, halide, and a charged ionic group; and wherein at least one of R, R', R" R'", R"", R""', R"""", and R""""' is other than H In an embodiment, the compound is:

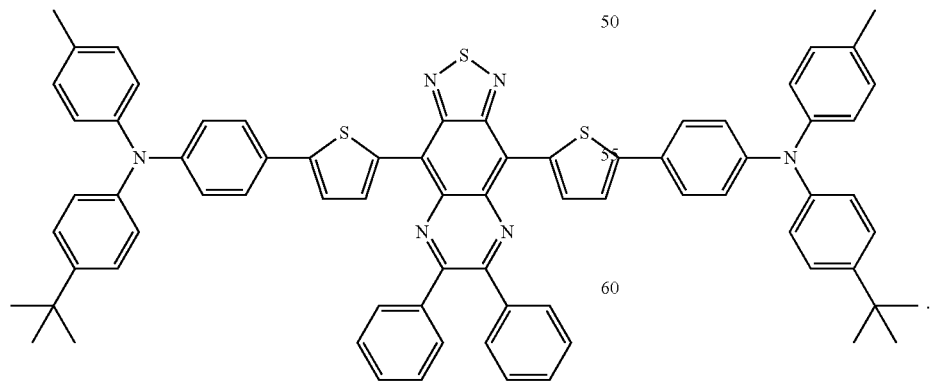

TPA-T-TQ

An exemplary reaction scheme for preparing the TPA-T-TQ compound is provided below:
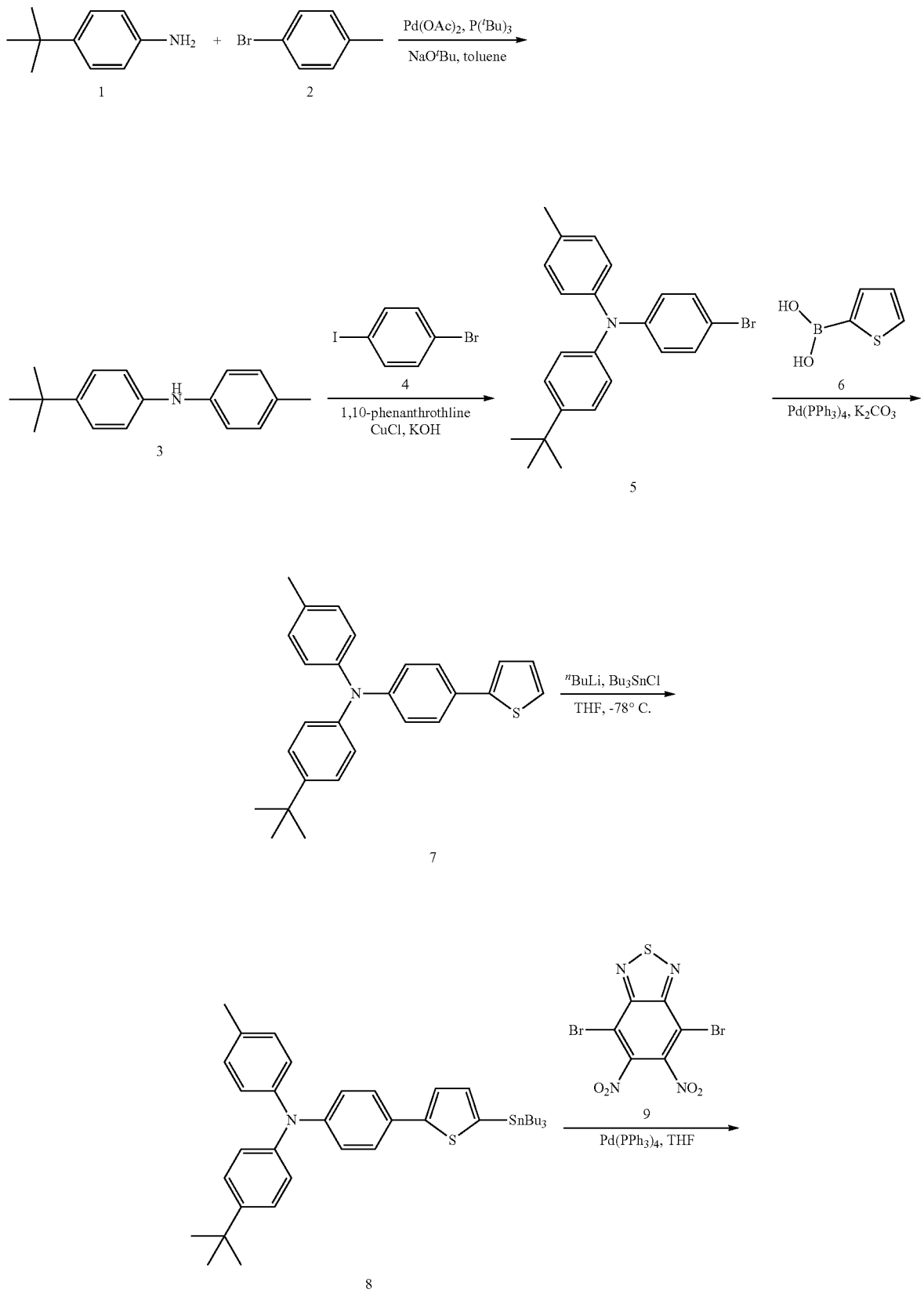

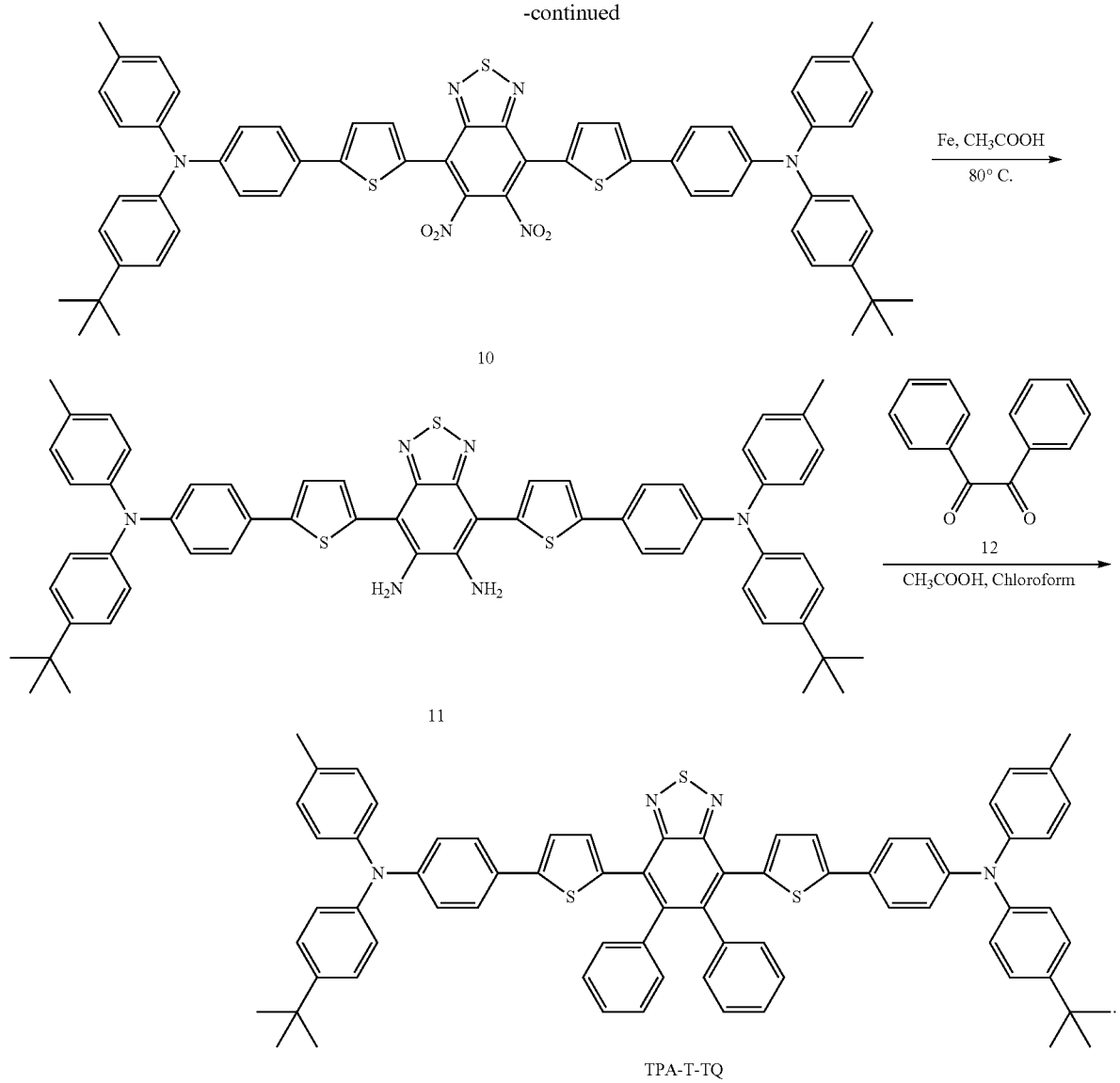

In an embodiment the compounds are provided as nanoparticles. The nanoparticles can be synthesized using an amphiphilic matrix as shown in the reaction scheme depicted in FIG. 8A and described in detail herein.

Identifying Tumor and Stopping or Inhibiting Tumor Growth

The present compounds can be administered to a patient as a contrast agent for locating a tumor site in the patient using in vivo imaging techniques, e.g., photoacoustic imaging. The compounds can be administered by intravenous injection, for example. As set forth in detail herein, in vivo imaging studies demonstrate that the compounds can serve as an effective probe for PAI in a high-contrast manner. Once the tumor site has been determined, the tumor site can be irradiated with near-infrared light which, when combined with the present compounds, can stop or inhibit the growth of the tumor. In an embodiment, the compounds can be administered to the patient six hours prior to PA imaging and PTT treatment of the tumor.

In vivo tumor growth kinetics with a xenograft 4T1 tumor-bearing mouse model reveal that PTT using the present compounds effectively suppresses and stops tumor growth. The present compounds demonstrate rapid temperature elevation in a tumor site under NIR light irradiation, which results in heat-caused tumor inhibition. As described herein, this superior antitumor efficacy is also confirmed by histological and immune-histochemical staining of tumor slices. Various functional and targeted groups can be introduced to the compounds to facilitate specific targeting of a desired biological species. According to an embodiment, one or more peptides can be conjugated to the present compounds.

As the present compounds are completely organic, these compounds show good biocompatibility, and no detectable side toxicity based on histological examinations and blood tests. The compounds demonstrate ultra-high stability and good photothermal/photoacoustic performance, making them promising candidates for in vivo diagnosis and therapy applications.

The present teachings are illustrated by the following examples.

EXAMPLES

Materials and Instruments $^1$H (400 MHz) and $^{13}$C (100 MHz) nuclear magnetic resonance (NMR) spectra were recorded on a Bruker AV 400 spectrometer by using CDCl$_3$ or DMSO-d$_6$ as the solvent. High-resolution mass spectra (HRMS) were measured on a GCT premier CAB048 mass spectrometer in MALDI-TOF mode. Thermogravimetric analysis (TGA) measurement was conducted on a TA TGA Q5000 with a heating rate of 10° C./min under nitrogen atmosphere. The UV-vis-NIR absorption spectra were performed on a PerkinElmer Lambda 365 spectrophotometer. The photoluminescence (PL) spectra were conducted using a Horiba Fluorolog-3 spectrofluorometer. Dynamic light scattering (DLS) was performed on a 90 plus particle size analyzer. Transmission electron microscopy (TEM) images were obtained on a JEM-2010F transmission electron microscope with an accelerating voltage of 200 kV.

Quantitative data were expressed as mean±standard deviation (SD). Statistical comparisons were made by ANOVA analysis and two-sample Student's t-test. P value<0.05 was considered statistically significant.

Example 1

Synthesis of TPA-T-TQ

4-(tert-Butyl)-N-(p-tolyl)aniline (3)

4-(tert-Butyl)aniline (1.94 g, 13 mmol), 1-bromo-4-methylbenzene (1.71 g, 10 mmol), sodium tert-butoxide (1.25 g, 13 mmol), and palladium (II) acetate (Pd(OAc)$_2$) (45 mg, 0.2 mmol) were added into a 100 mL two-necked round-bottom flask. The flask was vacuumed and purged with dry nitrogen three times. Then tri-tert-butylphosphine (P($^t$Bu)3, 0.25 mmol, 1 M toluene solution, 0.25 mL) and anhydrous toluene (50 mL) were added, and the resulting mixture was heated to reflux and stirred for 24 h in the absence of light. After cooling down to room temperature, water was added, and the mixture was extracted with dichloromethane. The organic phase was combined, and dried with MgSO$_4$. After the removal of the solvent under reduced pressure, the residue was purified by column chromatography on silica gel using dichloromethane/hexane (v/v 1:4) as the eluent to result in 4-(tert-butyl)-N-(p-tolyl)aniline as a colorless solid (75% yield). $^1$H NMR (400 MHz, CDCl$_3$, 25° C.) δ (ppm): 7.29 (d, 2H), 7.09 (d, 2H), 7.03-6.97 (m, 4H), 5.56 (br, 1H), 2.32 (s, 3H), 1.33 (s, 9H). $^{13}$C NMR (100 MHz, CDCl$_3$, 25° C.) δ (ppm): 143.48, 141.20, 140.93, 130.29, 129.83, 126.10, 118.19, 117.16, 34.14, 31.51, 20.67.

4-Bromo-N-(4-(tert-butyl)phenyl)-N-(p-tolyl)aniline (5)

4-(tert-Butyl)-N-(p-tolyl)aniline (1.68 g, 7 mmol), 1-bromo-4-iodobenzene (1.98 g, 7 mmol), 1,10-phenanthrolline (0.27 g, 1.5 mmol), copper (I) chloride (0.15 g, 1.5 mmol), and potassium hydroxide (1.68 g, 30 mmol) were added into a 100 mL two-necked round-bottom flask. The flask was vacuumed and purged with dry nitrogen three times. Then anhydrous toluene (50 mL) was added, and the resulting mixture was heated to reflux and stirred for 24 h. After cooling down to room temperature, water was added, and the mixture was extracted with dichloromethane. The organic phase was combined, and dried with MgSO$_4$. After the removal of the solvent under reduced pressure, the residue was purified by column chromatography on silica gel using dichloromethane/hexane (v/v 1:6) as the eluent to result in 4-bromo-N-(4-(tert-butyl)phenyl)-N-(p-tolyl)aniline as a white solid (73% yield). $^1$H NMR (400 MHz, CDCl$_3$, 25° C.) δ (ppm): 7.22 (d, 2H), 7.09-6.95 (m, 8H), 6.93 (s, 2H), 2.30 (s, 3H), 1.30 (s, 9H). $^{13}$C NMR (100 MHz, CDCl$_3$, 25° C.) δ (ppm): 145.52, 144.75, 142.74, 131.91, 130.01, 129.76, 126.14, 125.88, 124.88, 124.07, 123.77, 122.74, 34.21, 31.46, 20.80.

Thiophen-2-ylboronic acid (6)

Into a 100 mL two-necked round-bottom flask, thiophene (1.68 g, 20 mmol) and anhydrous THF (40 mL) were added. The flask was then vacuumed and purged with dry nitrogen three times. Then the mixture was cooled with dry ice-acetone to −78° C., and maintained for 15 min, followed by the addition of n-butyllithium ("BuLi, 2.5 M hexane solution, 8.8 mL, 22 mmol). The reaction mixture was stirred at −78° C. for 30 min before slowly warmed to −20° C., and stirred for another 30 min. Afterwards, the mixture was cooled to −78° C., and trisethylborate (2.5 mL, 22 mmol) was added. The mixture was stirred at −78° C. for another 1 h, and then slowly warmed to room temperature, and stirred overnight. The reaction mixture was then treated with aqueous HCl (1 M), and extracted with dichloromethane three times. The organic phase was combined, and dried with MgSO$_4$. After the removal of the solvent under reduced pressure, the product was further purified by recrystallization to give thiophen-2-ylboronic acid as a white solid (65% yield). $^1$H NMR (400 MHz, DMSO-d$_6$, 25° C.) δ (ppm): 8.20 (d, 2H), 7.74 (dd, 1H), 7.67 (dd, 1H), 7.17 (dd, 1H). $^{13}$C NMR (100 MHz, DMSO-do, 25° C.) δ (ppm): 136.41, 132.02, 128.54.

4-(tert-Butyl)-N-(4-(thiophen-2-yl)phenyl)-N-(p-tolyl)aniline (7)

4-Bromo-N-(4-(tert-butyl)phenyl)-N-(p-tolyl)aniline (1.97 g, 5 mmol), thiophen-2-ylboronic acid (0.64 g, 5 mmol), Pd(PPh$_3$)$_4$ (115 mg, 0.1 mmol), and K$_2$CO$_3$ (2.76 g, 20 mmol) were added into a 100 mL two-necked round-bottom flask. The flask was vacuumed and purged with dry nitrogen three times. Then anhydrous THF (40 mL) and water (10 mL) were added, and the mixture was heated to reflux and stirred for 24 h in the absence of light. After cooling down to room temperature, water was added, and the mixture was extracted with dichloromethane. The organic phase was combined, and dried with MgSO$_4$. After the removal of the solvent under reduced pressure, the residue was purified by column chromatography on silica gel using dichloromethane/hexane (v/v 1:5) as the eluent to result in 4-(tert-butyl)-N-(4-(thiophen-2-yl)phenyl)-N-(p-tolyl)aniline as a light yellow solid (81% yield). $^1$H NMR (400 MHz, CDCl$_3$, 25° C.) δ (ppm): 7.46-7.42 (m, 2H), 7.25-7.23 (m, 2H), 7.19 (d, 2H), 7.10-7.00 (m, 9H), 2.32 (s, 3H), 1.31 (s, 9H). $^{13}$C NMR (100 MHz, CDCl$_3$, 25° C.) δ (ppm): 147.65, 145.80, 145.03, 144.85, 144.54, 132.84, 129.96, 127.95, 127.71, 126.63, 126.09, 124.96, 123.84, 123.76, 122.75, 121.98, 34.31, 31.46, 20.87.

4-(tert-Butyl)-N-(p-tolyl)-N-(4-(5-(tributylstannyl)thiophen-2-yl)phenyl)aniline (8)

4-(tert-Butyl)-N-(4-(thiophen-2-yl)phenyl)-N-(p-tolyl)aniline (1.2 g, 3 mmol) was added into a 100 mL two-necked round-bottom flask. The flask was vacuumed and purged with dry nitrogen three times. Then anhydrous THF (50 mL) was added, and the resulting mixture was cooled with dry ice-acetone to −78° C., and maintained for 15 min, followed by the addition of n-butyllithium ("BuLi, 2.5 M hexane solution, 1.25 mL, 3.2 mmol). The mixture was stirred at −78° C. for 2 h. Afterwards, tri-n-butyltin chloride (0.9 mL, 3.3 mmol) was added, and the mixture was slowly warmed to room temperature, and stirred overnight. Water was added to quench the reaction, and the mixture was extracted with dichloromethane three times. The organic phase was combined, and dried with $MgSO_4$. After the removal of the solvent under reduced pressure, 4-(tert-butyl)-N-(p-tolyl)-N-(4-(5-(tributylstannyl)thiophen-2-yl)phenyl)aniline was obtained as a brownish oil, and it was used without further purification.

4,7-Dibromo-5,6-dinitrobenzo[c][1,2,5]thiadiazole (9)

The mixture of 4,7-dibromobenzo[c][1,2,5]thiadiazole (8.82 g, 30 mmol), sulfuric acid (60 mL), fuming sulfuric acid (20 mL), fuming nitric acid (50 mL) was stirred at 0° C. for 4 h to finish the nitration reaction. Then the mixture was poured into ice water (500 mL) slowly to get a suspension, and filtered through a Buchner funnel, washed with water several times, and dried in vacuum to get 4,7-dibromo-5,6-dinitrobenzo[c][1,2,5]thiadiazole as a light yellow powder (88% yield). $^{13}C$ NMR (100 MHz, DMSO-$d_6$, 25° C.) δ (ppm): 151.98, 144.13, 111.84.

4,4'-((5,6-Dinitrobenzo[c][1,2,5]thiadiazole-4,7-diyl)bis(thiophene-5,2-diyl))bis(N-(4-(tert-butyl)phenyl)-N-(p-tolyl)aniline) (10)

Figure 3:
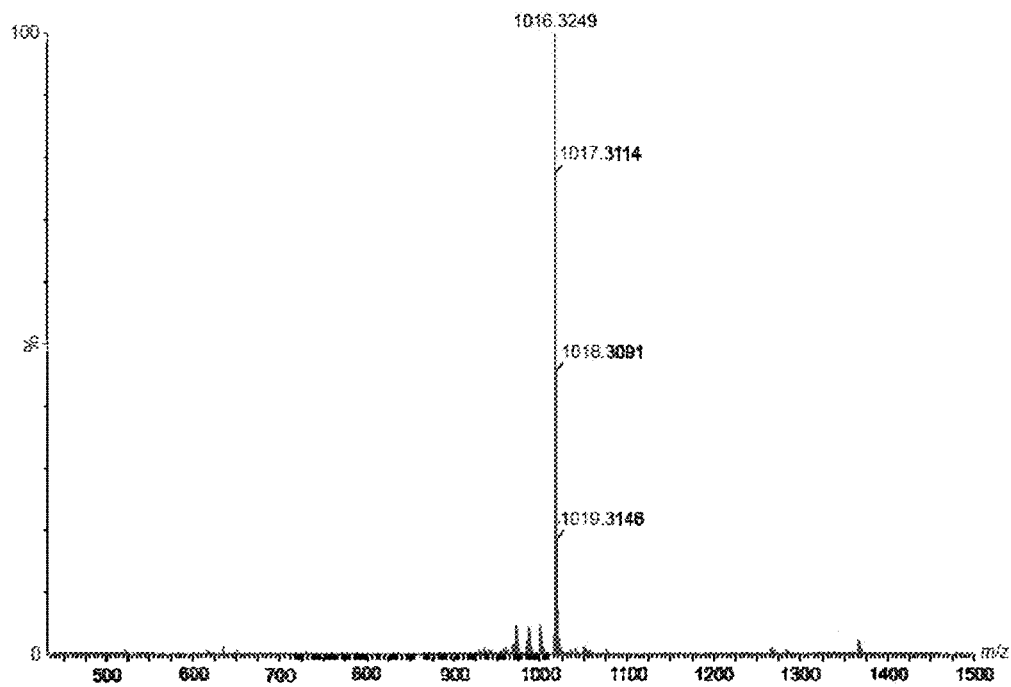
FIG. 3 depicts the HRMS of compound 10.

4-(tert-Butyl)-N-(p-tolyl)-N-(4-(5-(tributylstannyl)thiophen-2-yl)phenyl)aniline (2.06 g, 3 mmol), 4,7-dibromo-5,6-dinitrobenzo[c][1,2,5]thiadiazole (0.46 g, 1.2 mmol), and $Pd(PPh_3)_4$ (58 mg, 0.05 mmol) were added into a 100 mL two-necked round-bottom flask. The flask was vacuumed and purged with dry nitrogen three times. Then anhydrous THF (40 mL) was added, and the mixture was heated to reflux and stirred for 24 h in the absence of light. After cooling down to room temperature, water was added, and the mixture was extracted with dichloromethane. The organic phase was combined, and dried with $MgSO_4$. After the removal of the solvent under reduced pressure, the crude product was purified by column chromatography on silica gel using dichloromethane/hexane (v/v 1:3) as the eluent to result in 4,4'-((5,6-dinitrobenzo[c][1,2,5]thiadiazole-4,7-diyl)bis(thiophene-5,2-diyl))bis(N-(4-(tert-butyl)phenyl)-N-(p-tolyl)aniline) as a dark blue solid (79% yield). The $^1H$ NMR spectrum of compound 10 is depicted in FIG. 1. The $^{13}C$ NMR spectrum of compound 10 is depicted in FIG. 2. The HRMS of compound 10 is depicted in FIG. 3. $^1H$ NMR (400 MHz, CDCl$_3$, 25° C.) δ (ppm): 7.49 (m, 6H), 7.28 (m, 6H), 7.11 (m, 4H), 7.05 (m, 12H), 2.34 (s, 6H), 1.33 (m, 18H). $^{13}C$ NMR (100 MHz, CDCl$_3$, 25° C.) S (ppm): 152.02, 151.40, 148.86, 146.44, 144.61, 144.43, 141.20, 133.44, 132.18, 130.06, 127.53, 126.88, 126.21, 125.73, 125.38, 124.38, 122.80, 121.78, 120.28, 34.37, 31.44, 20.91. HRMS (MALDI-TOF, m/z): [M]$^+$ calcd for $C_{60}H_{52}N_6O_4S_3$, 1016.3212; found, 1016.3249.

4,7-Bis(5-((4-(tert-butyl)phenyl)(p-tolyl)amino) phenyl)thiophen-2-yl)benzo[c][1,2,5]thiadiazole-5,6-diamine (11)

4,4'-((5,6-Dinitrobenzo[c][1,2,5]thiadiazole-4,7-diyl)bis(thiophene-5,2-diyl))bis(N-(4-(tert-butyl)phenyl)-N-(p-tolyl)aniline) (0.92 g, 0.9 mmol), iron powder (1.1 g, 20 mmol) and acetic acid (50 mL) were suspended in a 100 mL round-bottom flask, and the mixture was heated to 80° C., and stirred for 4 h. After cooling down to room temperature, water was added, and the mixture was extracted with dichloromethane. The organic layer was washed with water and $NaHCO_3$ aqueous solution. The organic phase was combined, and dried with $MgSO_4$. After the removal of the solvent under reduced pressure, 4,7-bis(5-(44(4-(tert-butyl)phenyl)(p-tolyl)amino)phenyl)thiophen-2-yl)benzo[c][1,2,5]thiadiazole-5,6-diamine was obtained as a dark red solid and used without further purification.

4,4'-((6,7-Diphenyl-[1,2,5]thiadiazolo[3,4-g]quinoxaline-4,9-diyl)bis(thiophene-5,2-diyl))bis(N-(4-(tert-butyl)phenyl)-N-(p-tolyl)aniline) (TPA-T-TQ)

Figure 4:
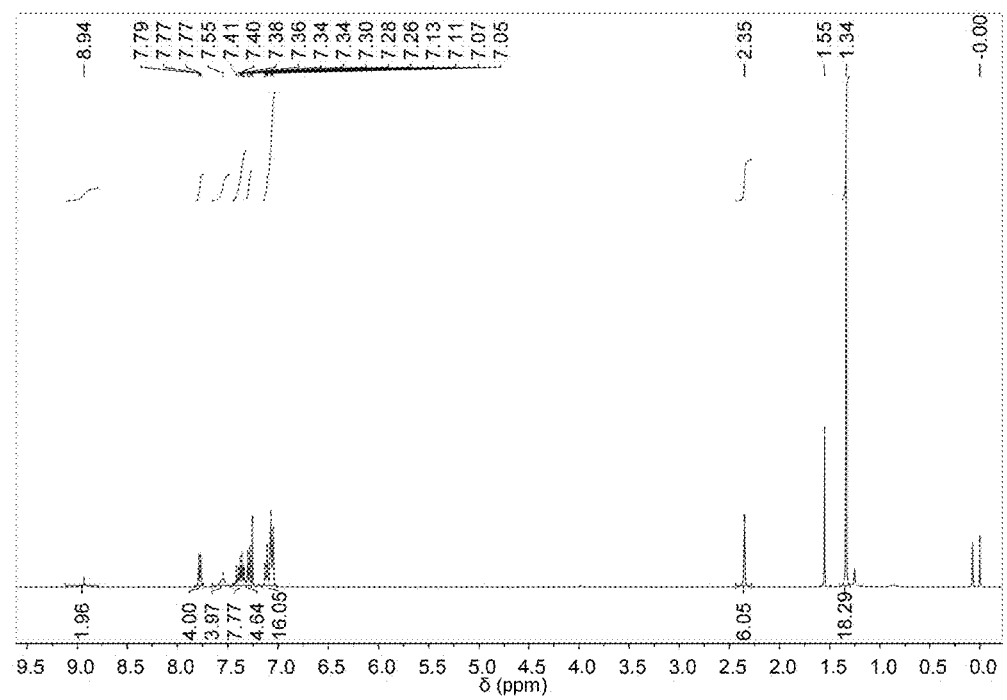
FIG. 4 depicts the $^1$H NMR spectrum of compound TPA-T-TQ in $CDCl_3$.
Figure 5:
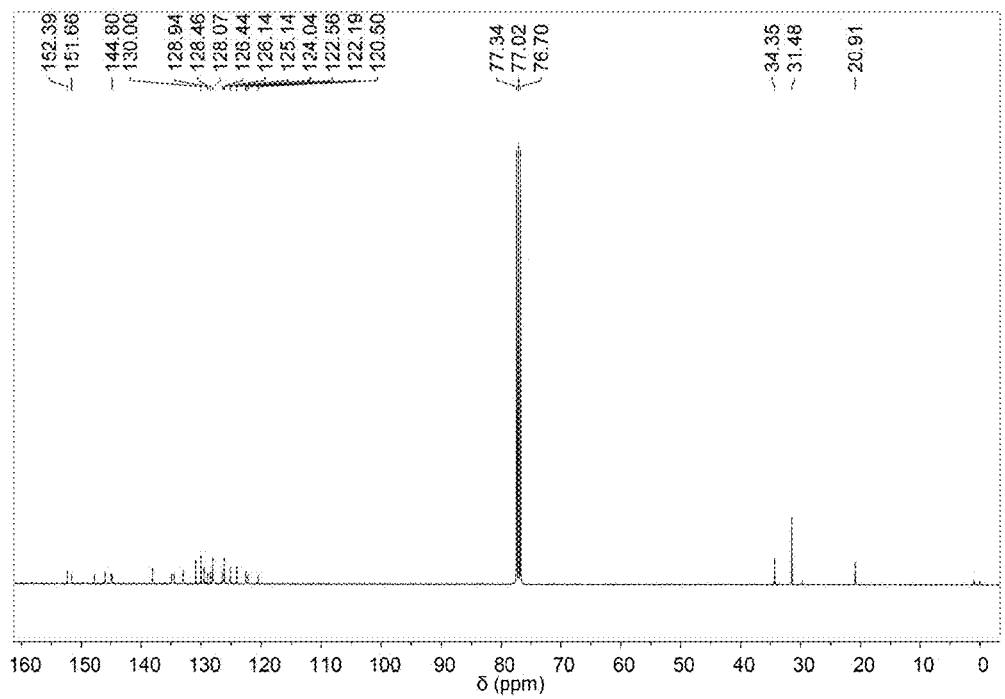
FIG. 5 depicts the $^{13}$C NMR spectrum of compound TPA-T-TQ in $CDCl_3$.
Figure 6:
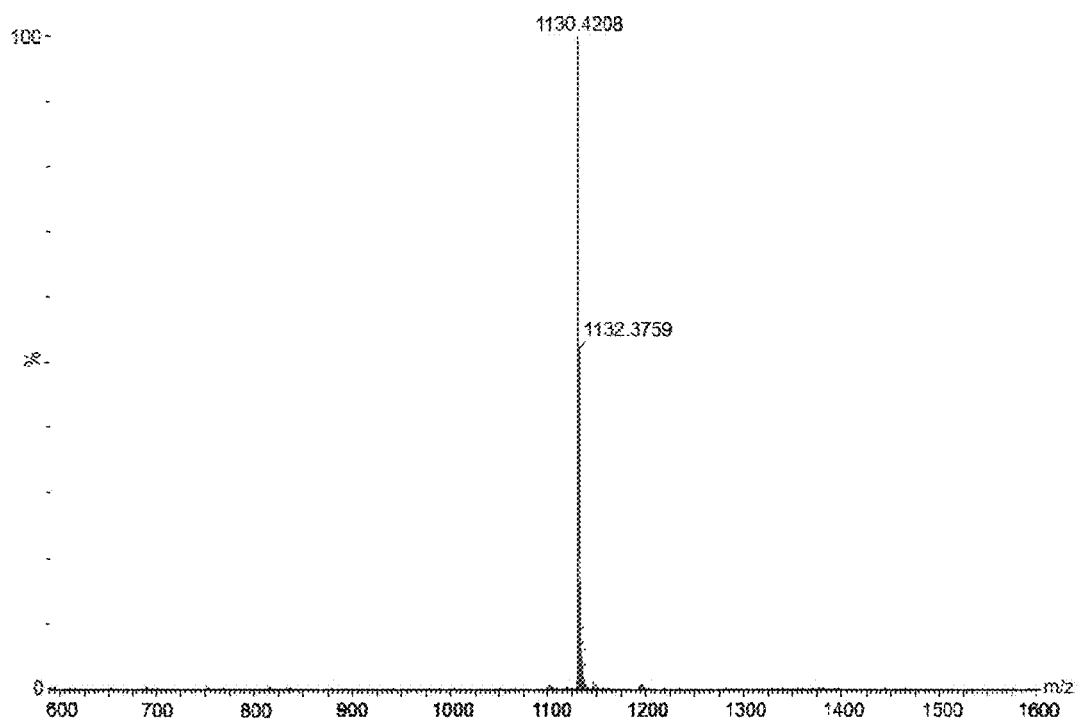
FIG. 6 depicts the HRMS of compound TPA-T-TQ.

4,7-bis(5-(4-((4-(tert-butyl)phenyl)(p-tolyl)amino)phenyl)thiophen-2-yl)benzo[c][1,2,5]thiadiazole-5,6-diamine (0.86 g, 0.9 mmol) was dissolved in the mixture of chloroform (20 mL) and acetic acid (20 mL) in a 100 mL round-bottom flask, and benzil (0.32 g, 1.5 mmol) was added. Then the mixture was heated to reflux and stirred for 12 h. After cooling down to room temperature, water was added, and the mixture was extracted with dichloromethane. The organic layer was washed with water and $NaHCO_3$ aqueous solution. The organic phase was combined, and dried with $MgSO_4$. After the removal of the solvent under reduced pressure, the crude product was purified by column chromatography on silica gel using dichloromethane/hexane (v/v 1:3) as the eluent to result in 4,4'-((6,7-diphenyl-[1,2,5]thiadiazolo[3,4-g]quinoxaline-4,9-diyl)bis(thiophene-5,2-diyl))bis(N-(4-(tert-butyl)phenyl)-N-(p-tolyl)aniline) as a yellow-green solid (76% yield). The $^1H$ NMR spectrum of TPA-T-TQ is depicted in FIG. 4. The $^{13}C$ NMR spectrum of TPA-T-TQ is depicted in FIG. 5. The HRMS of TPA-T-TQ is depicted in FIG. 6. $^1H$ NMR (400 MHz, CDCl$_3$, 25° C.) δ (ppm): 8.94 (br, 2H), 7.77 (m, 4H), 7.55 (br, 4H), 7.45-7.32 (m, 8H), 7.29 (d, 4H), 7.15-7.01 (m, 16H), 2.35 (s, 6H), 1.34 (s, 18H). $^{13}C$ NMR (100 MHz, CDCl$_3$, 25° C.) δ (ppm): 152.39, 151.66, 147.86, 145.95, 144.97, 144.80, 138.08, 134.90, 134.47, 132.98, 130.88, 130.00, 129.50, 128.94, 128.46, 128.07, 126.44, 126.14, 125.14, 124.04, 122.56, 122.19, 122.80, 120.50, 34.35, 31.48, 20.91. HRMS (MALDI-TOF, m/z): [M]$^+$ calcd for $C_{74}H_{62}N_6S_3$, 1130.4198; found, 1130.4208.

Example 2

Synthesis of TPA-T-TQ Organic Nanoparticles (ONPs)

Figures 8A, 8B, 8C, 8D, 8E:
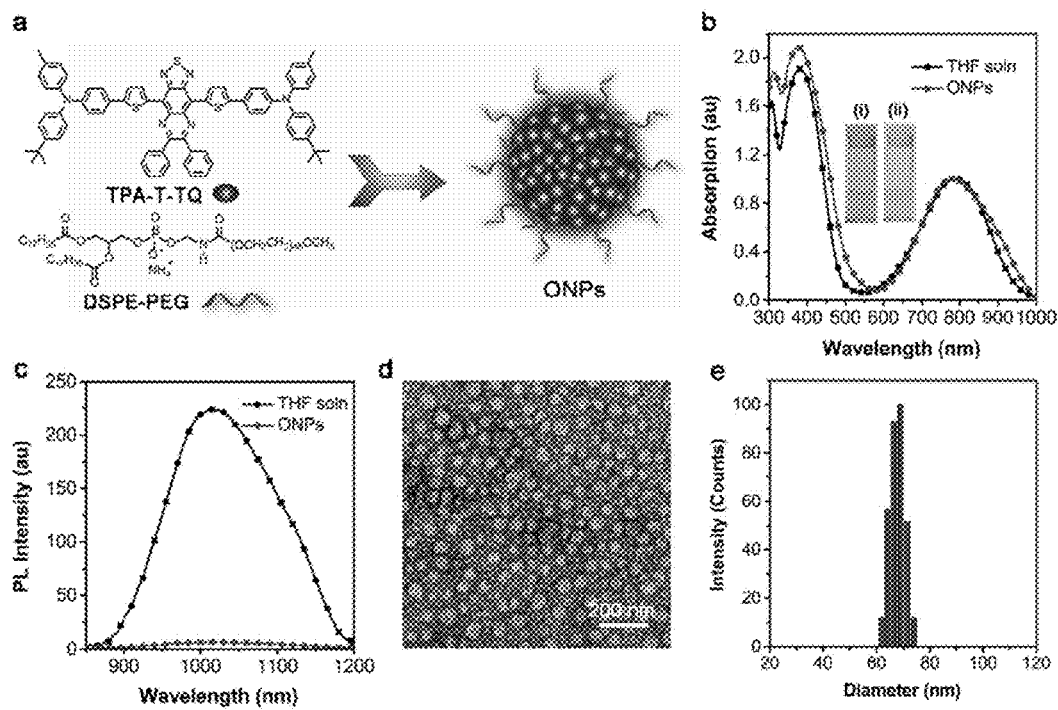
FIG. 8A depicts a schematic for preparing the organic small molecular nanoparticles through nanoprecipitation method.
FIG. 8B depicts the UV-vis-NIR absorption spectra of TPA-T-TQ in THF solution and the encapsulated ONPs in water.
FIG. 8C depicts the photoluminescence (PL) spectra of TPA-T-TQ in THF solution and the encapsulated ONPs in water.
FIG. 8D depicts the TEM image of the TPA-T-TQ ONPs.
FIG. 8E depicts the DLS profile of the TPA-T-TQ ONPs.

1 mL of tetrahydrofuran (THF) solution containing 1 mg of TPA-T-TQ compound, and 2 mg of 1,2-distearoyl-sn-glycero-3-phosphoethanolamine-N-[methoxy(polyethylene glycol)-2000 (DSPE-PEG$_{2000}$) was poured into 10 mL of deionized water. The mixture was sonicated for 2 min using a microtip probe sonicator at 12 W output (XL2000, Misonix Incorporated, NY). The residue THF solvent was evaporated by violent stirring of the suspension at room temperature in fume hood overnight, and a colloidal solution was obtained and directly used. FIG. 8A depicts a schematic for preparing the organic small molecular nanoparticles using the nanoprecipitation method. FIG. 8B depicts the UV-vis-NIR absorption spectra of TPA-T-TQ in THF solution and the encapsulated ONPs in water. The inset shows the photographs of (i) the TPA-T-TQ THF solution, and (ii)

the as-prepared ONPs in water. FIG. 8C depicts the photoluminescence (PL) spectra of TPA-T-TQ in THF solution and the encapsulated ONPs in water. FIG. 8D depicts the TEM image of the TPA-T-TQ ONPs. FIG. 8E depicts the DLS profile of the TPA-T-TQ ONPs. The nanoparticles were negatively stained with uranyl acetate.

Example 3

Photo- and RONS-Stability Studies

For the photostability study, PBS solutions (pH 7.4) of TPA-T-TQ ONPs and ICG were irradiated under 808-nm laser (0.8 W/cm$^2$), and the absorption spectra were measured at different time points. For the anti-photobleaching study, the temperatures of the sample solutions were recorded during five circles of heating and cooling. In one heating-cooling circle, the NIR laser first irradiated the samples for 5 min to reach a steady state, then the laser was removed and the samples were naturally cooled down to ambient temperature in 6 min.

Figure 7:
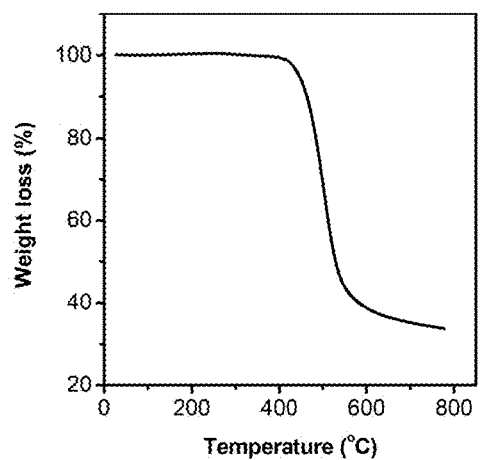
FIG. 7 depicts the Thermogravimetric analysis (TGA) curve of TPA-T-TQ.
Figures 9A, 9B, 9C, 9D, 9E, 9F, 9G, 9H, 9I:
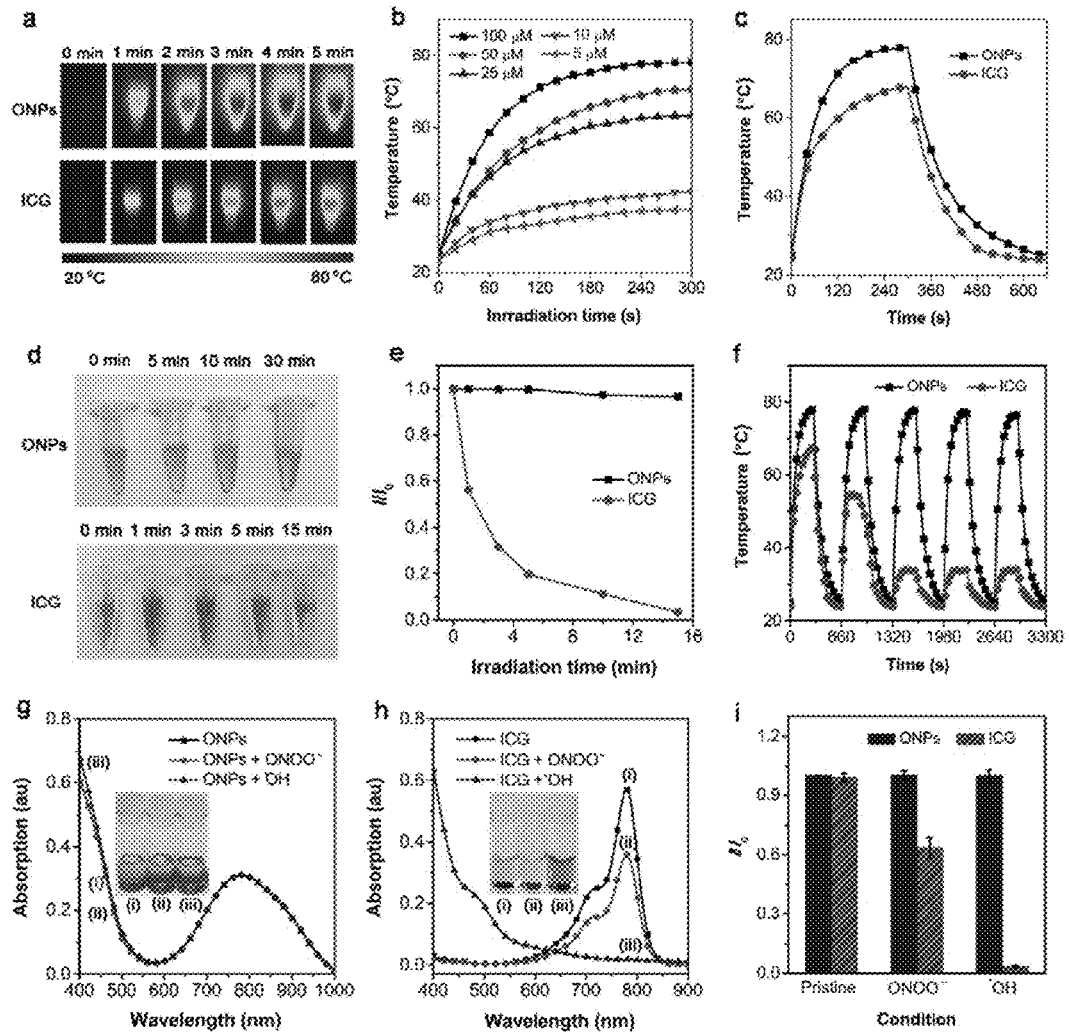
FIG. 9A depicts IR thermal images of the ONPs and ICG in PBS solutions (100 μM) under 808-nm laser irradiation (0.8 W/cm$^2$) for different times.
FIG. 9B depicts a graph showing photothermal conversion behavior of TPA-T-TQ ONPs at different concentrations (5-100 μM) under 808 nm light irradiation at a power intensity of 0.8 W/cm$^2$.
FIG. 9C depicts a graph comparing the photothermal conversion behavior of TPA-T-TQ ONPs and ICG in PBS solution at the same concentration (100 μM) (the 808-nm light (0.8 W/cm$^2$) was irradiated for 5 min).
FIG. 9D depicts photographs of the ONPs and ICG in PBS solutions after 808 nm light irradiation for different times.
FIG. 9E depicts a plot of $I/I_0$ versus various irradiation time (I and $I_0$ are the maximal NIR absorption intensity of ONPs/ICG in PBS solutions after and before laser irradiation, respectively).
FIG. 9F depicts a plot showing anti-photobleaching property of ONPs and ICG (100 μM) during five circles of heating-cooling processes (the laser used for irradiation was 808-nm light with a power density of 0.8 W/cm$^2$).
FIG. 9G depicts absorption spectra of TPA-T-TQ ONPs in PBS solution before and after 400 μM of ONOO$^-$ and .OH were added for 1 min (inset shows photograph of the solution of ONPs before and after the addition of RONS).
FIG. 9H depicts absorption spectra of ICG in PBS solution before and after 400 μM of ONOO$^-$ and .OH were added for 1 min (inset shows photograph of the solution of ICG before and after the addition of RONS).
FIG. 9I depicts a plot of $I/I_0$ versus RONS (ONOO$^-$ and .OH). I and $I_0$ are the maximal NIR absorption intensity of ONPs/ICG in PBS solutions in the presence and absence of RONS, respectively.

For the RONS-stability study, two kinds of RONS were used, i.e., ONOO$^-$ and .OH, which were prepared according to the literature. The absorption and photoluminescence spectra were recorded before and after addition of 0.4 mM of RONS. The stabilities of the contrast agents in terms of thermal and photothermal stabilities as well as photobleaching and RONS resistances are crucial for PAI/PTT applications in vivo because incorrect or misleading signals, weakened therapeutic efficacy, and harmful side effects can result if the structure of the agent is destroyed, especially in living systems. Thermogravimetric analysis (TGA) was first carried out to measure the thermal stability of TPA-T-TQ. The decomposition temperature for 5% weight loss of TPA-T-TQ was above 400° C. (FIG. 7), suggesting excellent thermal stability. Then the photostability of TPA-T-TQ ONPs was evaluated along with ICG under continuous 808 nm laser irradiation (0.8 W/cm$^2$) by recording the apparent colors and absorption spectra after laser irradiation for different times. FIG. 9A depicts IR thermal images of the ONPs and ICG in PBS solutions (100 µM) under 808-nm laser irradiation (0.8 W/cm$^2$) for different times. FIG. 9B depicts a graph showing photothermal conversion behavior of TPA-T-TQ ONPs at different concentrations (5-100 µM) under 808 nm light irradiation at a power intensity of 0.8 W/cm$^2$. FIG. 9C depicts a graph comparing the photothermal conversion behavior of TPA-T-TQ ONPs and ICG in PBS solution at the same concentration (100 µM) (the 808-nm light (0.8 W/cm$^2$) was irradiated for 5 min)

As shown in FIGS. 9D and 9E, the colors and absorption spectra of TPA-T-TQ ONPs are nearly unchanged during 15 min NIR light irradiation duration, whereas the blue-green color of ICG solution gradually disappears, and the maximal absorption intensity nearly drops to zero after being exposed to the NIR light for 15 min. Noteworthy is that the optical properties of TPA-T-TQ ONPs are identical to the original state even after continuous laser illumination (0.8 W/cm$^2$) for an hour. Then, the anti-photobleaching properties of TPA-T-TQ ONPs and ICG were evaluated by alternative heating and cooling processes (the NIR laser first irradiated the samples for 5 min to heat them up, then the laser was removed, and the samples were naturally cooled down to ambient temperature in 6 min). Interestingly, during five circles of heating and cooling processes, the photothermal conversion ability of the ONPs shows negligible change, while the temperature elevation of ICG dramatically dropped to about 20% (ΔT~10° C.) of the original value (ΔT~44° C.) after two circles of heating-cooling processes (FIG. 9F). These results provide solid confirmation that TPA-T-TQ ONPs possess superior resistance to photobleaching compared to the existent organic small molecules.

Figure 10:
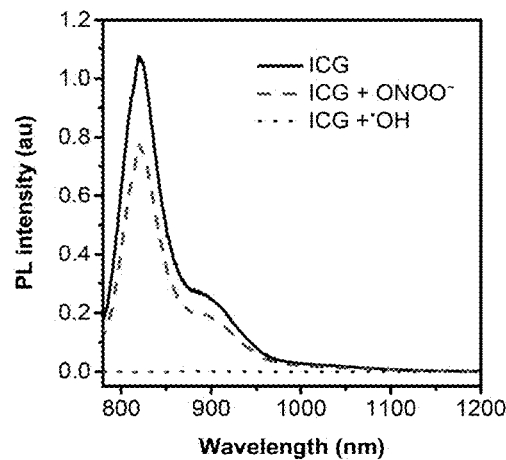
FIG. 10 depicts the photoluminescence (PL) spectra of ICG in water before and after the addition 0.4 mM of ONOO$^-$ and .OH for 1 min.

Another important issue related to in vivo applications is the physiological stability against highly reactive molecules such as RONS. RONS are a kind of signaling molecules which are necessary to regulate physiological functions, but are overproduced as a result of the presence of various diseases including inflammation, cancers, and cardiovascular diseases. For cancer diagnosis and treatment, it is considerably vital to use RONS-resistant agents to get reliable imaging signal and therapy efficacy. Therefore, the stability of TPA-T-TQ ONPs and ICG in the presence of two kinds of RONS, peroxynitrite (ONOO$^-$) and hydroxyl radical (.OH), were measured under physiological conditions. The absorption spectra and photographic solutions of TPA-T-TQ ONPs and ICG before and after the treatment of RONS reagents are depicted in FIGS. 9G and 9H, respectively. After the addition of ONOO$^-$ and .OH, the maximal absorption intensity of ICG (at 780 nm) drops to about 60% and 4% relative to the original value, respectively. In marked contrast, there is nearly no change in the absorption spectra and solution appearance of the ONPs after adding each RONS (FIG. 9I). FIG. 10 depicts the photoluminescence (PL) spectra of ICG in water before and after the addition 0.4 mM of ONOO$^-$ and .OH for 1 min.

Example 4

Photothermal Performance

The PBS solution (pH 7.4) of TPA-T-TQ ONPs and ICG in different concentrations were continuously exposed to NIR laser of 808 nm with a power intensity of 0.8 W/cm$^2$ for 5 min. The temperature was measured every 20 s and stopped until the temperature nearly reached a plateau. The corresponding IR thermal images were also recorded. To evaluate the photothermal conversion property, we quantitatively measured the temperature change of TPA-T-TQ ONP solution at different concentrations as a function of 808 nm laser (0.8 W/cm$^2$) irradiation time. As depicted in FIG. 9B, temperature increases very fast initially, and reaches a plateau after 3 min laser irradiation. It is noted that the eventual temperature at the plateau depends on the ONP concentration. The temperature increase of ONPs and ICG solutions upon exposure to 808 nm laser irradiation was compared. As displayed in FIG. 9C, the TPA-T-TQ ONPs (ΔT~53° C. in 5 min) exhibit much higher plateau temperature and faster temperature rise rate than ICG (ΔT~43° C. in 5 min), revealing superior photothermal conversion behavior of the ONPs. The difference in temperature elevation of the two samples at various irradiation times can be intuitively visualized from the infrared (IR) thermal images (FIG. 9A).

Example 5

Animal Model

To establish the xenograft 4T1 tumor-bearing mouse model, murine 4T1 breast cancer cells (1×10$^6$) suspended in 50 µL of RPMI-1640 medium were subcutaneously injected into the right axillary space of each mouse. After about 7 days, mice with tumor volumes at about 80-120 mm$^3$ were used.

Example 6

In Vivo Photoacoustic Imaging

Figures 11A, 11B, 11C, 11D:
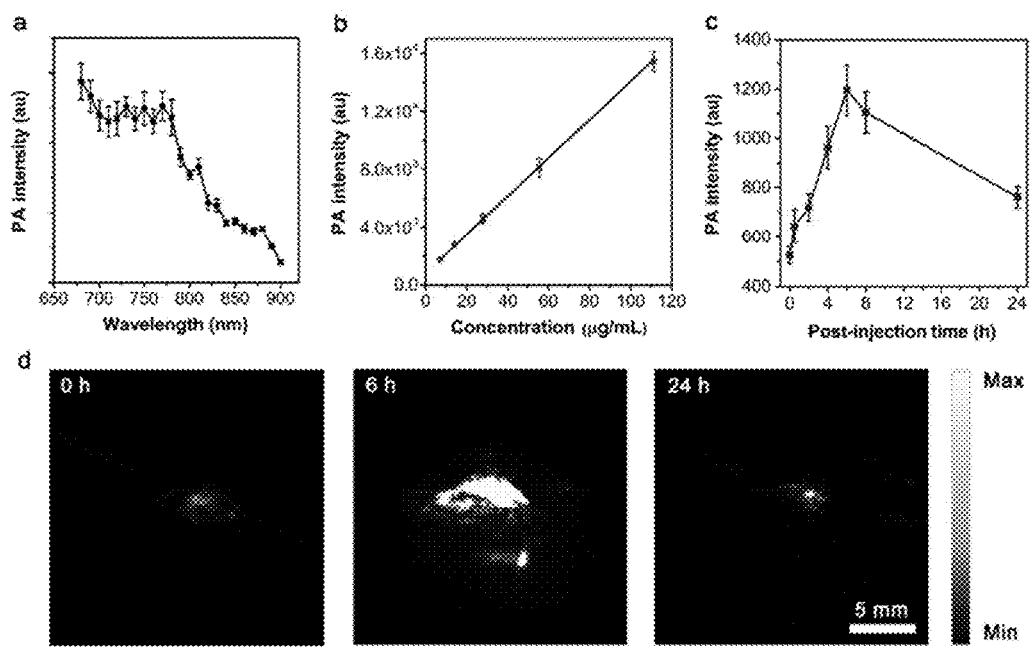
FIG. 11A depicts the PA spectrum of TPA-T-TQ ONPs in PBS solution (110 μg/mL based on TPA-T-TQ).
FIG. 11B depicts PA amplitudes of TPA-T-TQ ONPs at 770 nm as a function of TPA-T-TQ concentration.
FIG. 11C depicts PA intensity at the tumor site as a function of post-injection time.
FIG. 11D depicts PA images of tumor site after systemic administration of TPA-T-TQ ONPs for designated time intervals.

PA images were acquired at 770 nm at designated time intervals post ONPs injection. The in vivo PAI by intravenous injection of the TPA-T-TQ ONPs into xenograft 4T1 tumor-bearing nude mice was investigated. Before ONP administration (0 h), there is a weak PA signal at 770 nm probably attributed to the absorption of endogenous melanin and hemoglobin in the NIR spectral region. FIG. 11A depicts the PA spectrum of TPA-T-TQ ONPs in PBS solution (110 μg/mL based on TPA-T-TQ). FIG. 11B depicts PA amplitudes of TPA-T-TQ ONPs at 770 nm as a function of TPA-T-TQ concentration.

Compared with the PA image of the tumor at 0 h, the PA brightness of the tumor site after intravenous injection of TPA-T-TQ ONPs significantly increases over time, which reaches a maximum at 6 h post-injection (FIG. 11C), indicating that 6 h post-injection is the optimized time point for PA imaging and PTT treatment of tumor. The time-dependent PA images of tumors are presented in FIG. 11D. The PA signal at 6 h is 2.4-fold higher as compared to that of the tumor background, indicating the prominent enhanced permeability and retention (EPR) effect of the ONPs, which leads to their efficient accumulation in the tumor tissue.

Example 7

In Vivo Photothermal Therapy

The xenograft 4T1 tumor-bearing mice were randomly divided into 4 groups (n=6 per group), which were named "Only Saline", "Saline+Laser", "Only ONPs", and "ONPs+Laser", respectively. For "Only Saline" and "Only ONPs" groups, saline and TPA-T-TQ ONPs (250 μg/mL based on TPA-T-TQ) were injected into 4T1 tumor-bearing mice via the tail vein, respectively, without subsequent laser irradiation. For "Saline+Laser" and "ONPs+Laser" groups, after intravenous injection of saline and TPA-T-TQ ONPs (250 μg/mL based on TPA-T-TQ) for 6 h, respectively, the tumors of mice in each group were continuously irradiated with 808 nm laser (0.5 mW/cm$^2$) for 5 min. After a variety of treatments, the tumor volumes and mouse body weights were measured every other day for 16 days. The tumor volume was calculated by the following equation: Volume=Width$^2$×Length/2.

The PTT capability of the ONPs was validated with the xenograft 4T1 tumor mouse model. Tumor-bearing mice were randomly assigned to 4 groups, which were named "Only Saline", "Saline+Laser", "Only ONPs", and "ONPs+Laser", respectively. For "Only Saline" and "Only ONPs" groups, Saline and TPA-T-TQ ONPs (250 μg/mL based on TPA-T-TQ) were injected into 4T1 tumor-bearing mice via the tail vein, respectively, without subsequent laser irradiation. For "Saline+Laser" and "ONPs+Laser" groups, after intravenous injection of saline and TPA-T-TQ ONPs (250 μg/mL based on TPA-T-TQ) for 6 h, respectively, the tumors of mice in each group were continuously irradiated with 808 nm laser (0.5 mW/cm$^2$) for 5 min. Firstly, to verify that TPA-T-TQ ONP is able to generate heat with laser irradiation in living mice, the tumor temperatures of "ONPs+Laser"-treated and "Saline+Laser"-treated mice were monitored by IR thermography at different laser irradiation time scales.

Figures 12A, 12B, 12C, 12D:
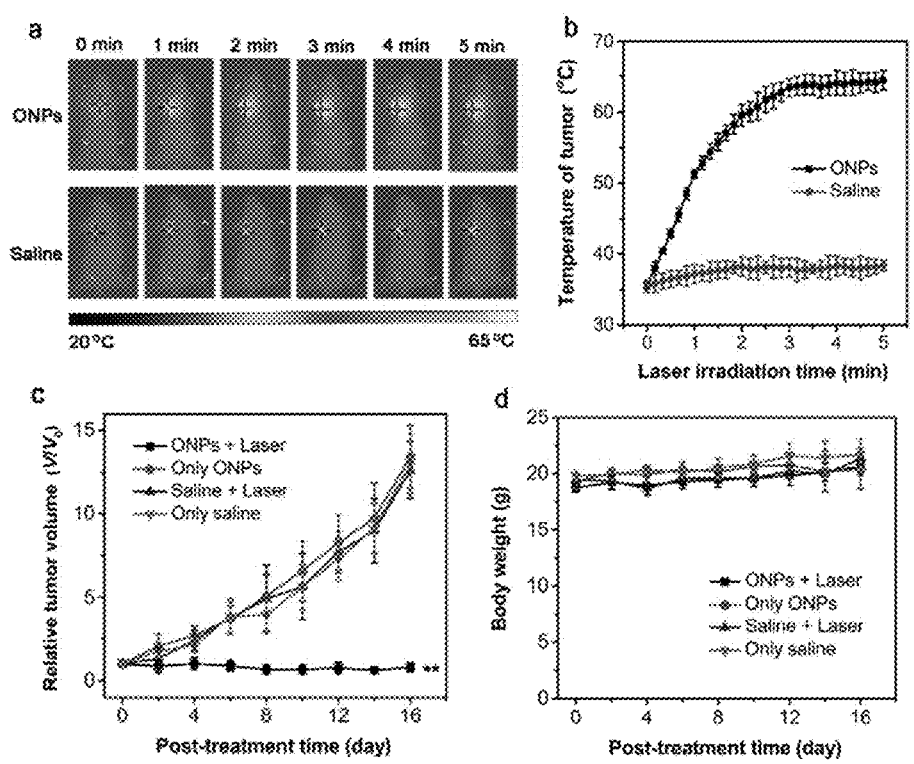
FIG. 12A depicts IR thermal images of 4T1 tumor-bearing mice under 808 nm laser irradiation (0.5 W/cm2) for different time points.
FIG. 12B depicts a graph showing the mean temperature of tumors as a function of the 808 nm laser (0.5 W/cm$^2$) irradiating time (laser irradiation was performed post 6 h intravenous administration of TPA-T-TQ ONPs or saline for (a) and (b)).
FIG. 12C depicts a graph showing tumor growth curves (of different treatment groups of mice (** represents P<0.01, in comparison between "ONPs+Laser" group and other treatment groups).
FIG. 12D depicts a graph showing body weight changes of different treatment groups of mice.

As depicted in FIGS. 12A and 12B, the tumors from mice in the "Saline+Laser" group exhibit little temperature elevation (ΔT~2.5° C.) upon NIR light exposure for 5 min, implying that laser irradiation alone would have negligible effect on heat-caused tumor inhibition. In comparison, fast temperature elevation is observed from the tumors in the "ONPs+Laser"-treated mice, as evidenced by the tumor temperature raising from 36° C. to a plateau of about 64° C. in 3 min light exposure. Such in vivo temperature rise rate and elevated temperatures are comparable to the best light-to-heat conversion performances achieved by currently available organic photothermal agents. These results illuminate that the TPA-T-TQ ONPs can result in a rapid temperature elevation in a tumor site under NIR light irradiation, representing an efficient agent for tumor PTT in living organisms.

The in vivo antitumor efficacy of "ONPs+Laser" through a single PTT was investigated by monitoring the tumor volumes for 16 days. As presented in FIG. 12C, the treatment of the "Saline+Laser" group totally fails to suppress the tumor growth as compared to the control group ("Only Saline"), indicating that pure 808 nm laser irradiation does not possess any antitumor effect. Moreover, the tumor growth kinetics from mice in the "Only ONPs" group is also similar to that in the "Only Saline" group, suggesting that the ONPs taken by themselves have negligible active behavior against cancer. Dramatically, as compared to the other three groups with fast-growing tumor volumes, the "ONPs+Laser" group shows amazing antitumor efficacy. The average tumor volume on day 16 in the "ONPs+Laser" group is even slightly smaller than that on day 0, suggesting that the PTT by TPA-T-TQ ONPs is capable of resulting in tumor growth stoppage, which is indeed efficacious on tumor suppression. The mice in each treatment group were also weighed every other day during a 16-day study duration. As shown in FIG. 12D, no obvious body weight loss is observed in mice of the "Only ONPs", "Saline+Laser", and "ONPs+Laser" groups when compared with the control group, suggesting the low toxic side effect of the treatment of "ONPs+Laser".

Example 8

Histological Studies

Figures 13A, 13B:
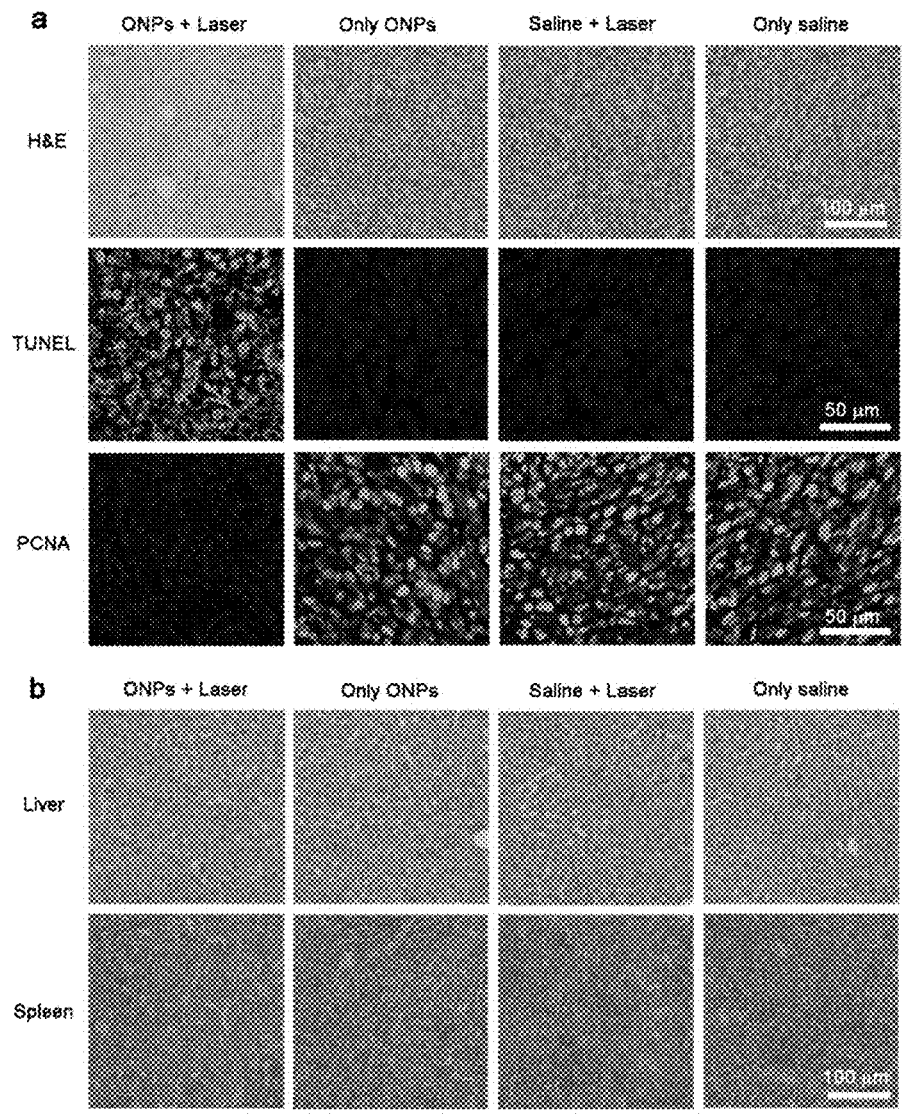
FIG. 13A shows histological H&E, fluorescence TUNEL and PCNA staining of tumor slices at day 16 after treatment with ONPs and laser, only ONPs, saline and laser, and only saline, respectively.
FIG. 13B shows histological H&E staining for livers and spleens on day 16 after the treatment with ONPs and laser, only ONPs, saline and laser, and only saline, respectively.

Sixteen days after photothermal treatment, the above-mentioned four groups of mice were sacrificed and tumors and important normal organs were excised, sliced and stained. The fluorescent PCNA staining was conducted following common immunohistochemical steps. The fluorescent TUNEL staining was conducted following manual instruction of the DeadEnd fluorometric TUNEL system kit (Promega, USA). For hematoxylin and eosin (H&E) staining, the tissues of the mice were fixed in 4% formalin, processed into paraffin, and sectioned at 5 μm thickness. The slices were examined by a digital microscope (Leica QWin) (FIG. 13A). To study whether TPA-T-TQ ONPs cause in vivo toxicity, the livers and spleens of mice in each treatment group were also excised and sectioned for H&E staining at the end time point, as it is generally accepted that nanomaterials tend to be enriched in reticuloendothelial system (RES) organs including liver and spleen. No noticeable tissue damage and/or inflammatory lesion were found in the liver and spleen organs from all the treatment groups of mice (FIG. 13B).

Example 9

Serum Biochemistry Assay and Complete Blood Count

Figure 14A:
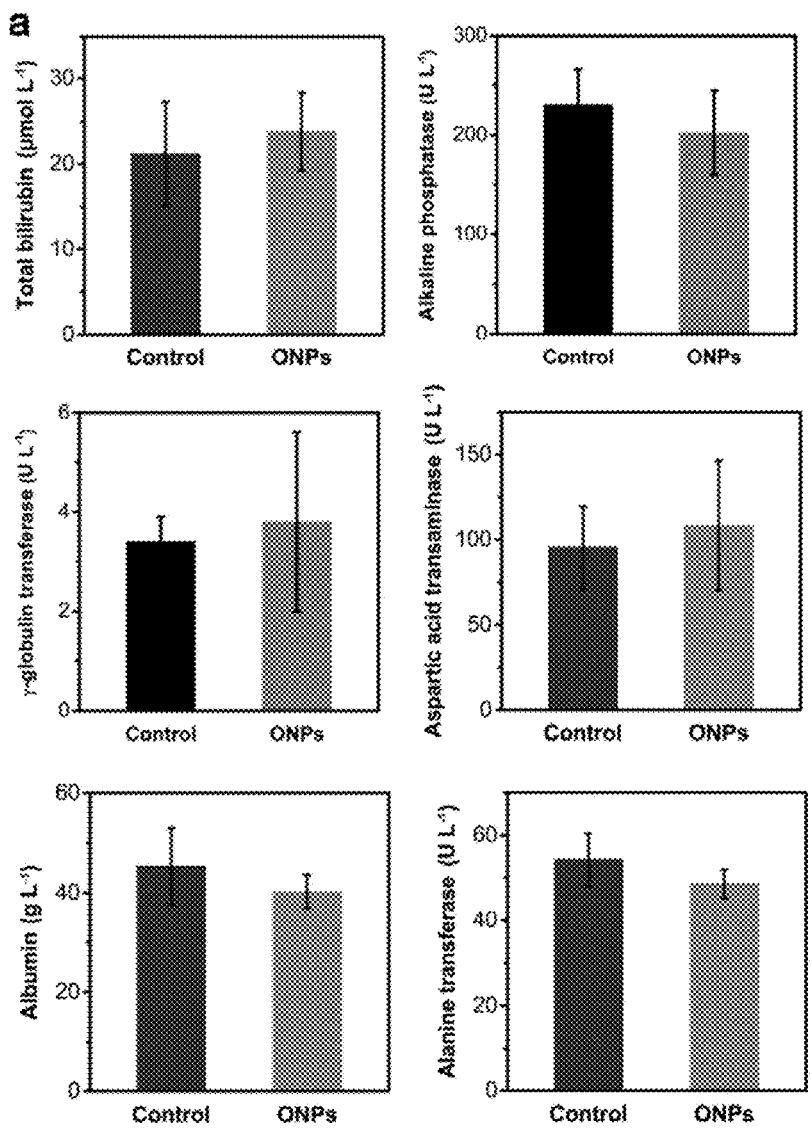
FIG. 14A depicts graphs summarizing blood biochemistry data of healthy Balb/c mice treated with TPA-T-TQ ONPs for 7 days.
Figure 14B:
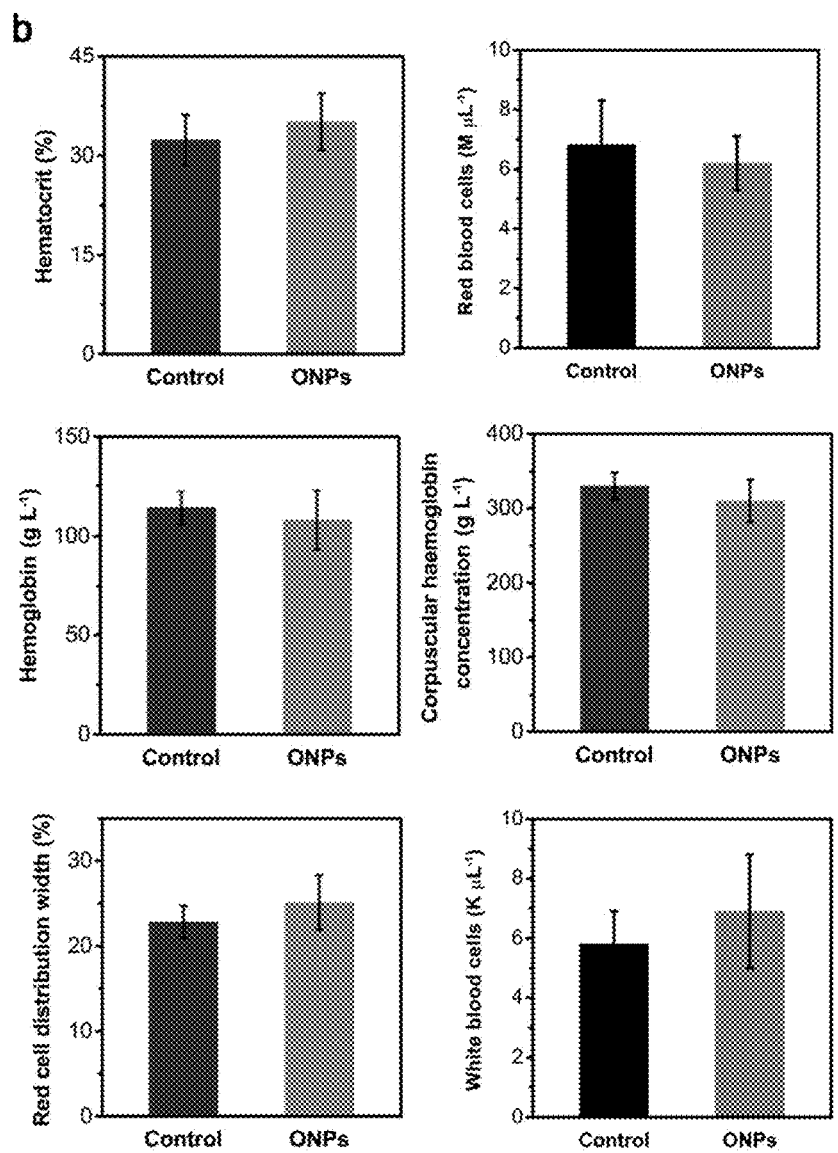
FIG. 14B depicts graphs summarizing hematology data of healthy Balb/c mice treated with TPA-T-TQ ONPs for 7 days (the untreated mice were used as the control).

Healthy Balb/c mice were randomly divided into 2 groups (n=3 per group). 150 μL of TPA-T-TQ ONPs (250 μg/mL based on TPA-T-TQ) was intravenously (i.v.) injected into one group of mice. For the other group, no treatment was performed. After one week, blood was collected for all mice and then detected using an automated hematology analyzer. In order to further investigate the potential toxicology of TPA-T-TQ ONPs, healthy Balb/c mice intravenously administrated with TPA-T-TQ ONPs (250 μg/mL based on TPA-T-TQ) as well as untreated healthy mice received serum biochemistry assay and complete blood count on day 7 post-injection. The liver function indicators including alanine aminotransferase (ALT), aspartic acid transaminase (AST), albumin (ALB), total bilirubin (TBIL), alkaline phosphatase (ALP), and γ-globulin transferase (GGT), all measured normal (FIG. 14A), and revealed no obvious hepatic and kidney disorders of "ONPs+Laser"-treated mice. The assay of complete blood panel including white blood cells (WBC), lymphocyte (LYM), hematocrit (HCT), hemoglobin (Hgb), red blood cells (RBC), red cell distribution width (RDW), corpuscular hemoglobin concentration (CHC), platelets (PLT), as well as mean platelet volume (MPV) indicated that there are no statistical differences in these indicators between ONPs and untreated groups (FIGS. 14A-14B). Further, considering the negligible influences of TPA-T-TQ ONPs on mouse body weight FIG. 12D and the health of important normal organs FIG. 13B, it is reasonable to conclude that the TPA-T-TQ ONP is a highly biocompatible phototheranostic nanoagent which induces no noticeable side effect to living mice.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:
1. A theranostic agent of the following structural formula:

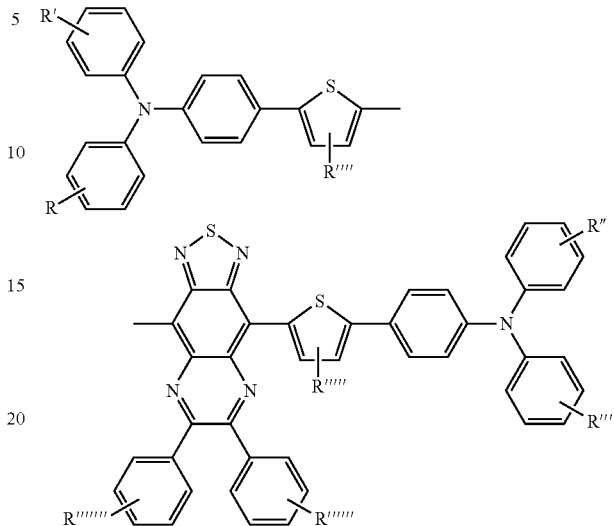

wherein each of R, R' R", R''', R'''', R''''', and R'''''' is unsubstituted or substituted, and is selected from the group consisting of F, H, alkyl, unsaturated alkyl, heteroalkyl, cycloalkyl, heterocycloalkyl, aryl, heteroaryl, carboxyl group, amino group, sulfonic group, alkylthio, and alkoxy group; and wherein at least one of R, R', R" R''', R'''', R''''', and R'''''' is other than H.

* * * * *